(12) United States Patent
Skern et al.

(10) Patent No.: US 6,180,385 B1
(45) Date of Patent: *Jan. 30, 2001

(54) PICORNAVIRUS I PROTEINASE AND METHODS OF MAKING AND USING THEREOF

(75) Inventors: Timothy Skern, Hainburg/Donau; Regina Kirchweger, Oed/Amstetten; Elisabeth Ziegler, Vienna; Dieter Blaas, Vienna; Hans-Dieter Liebig, Vienna, all of (AT); Barry J. Lamphear, Shreveport, LA (US); Debra Waters, Lafayette, LA (US); Robert E. Rhoads, Shreveport, LA (US); Wolfgang Sommergruber, Purkersdorf; Horst Ahorn, Weigelsdorf, both of (AT)

(73) Assignee: Boehringer Ingelheim Vetmedica GmbH, Ingelheim am Rhein (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/736,915

(22) Filed: Oct. 25, 1996

Related U.S. Application Data

(63) Continuation of application No. 08/279,152, filed on Jul. 22, 1994, now abandoned.

(51) Int. Cl.[7] ............................... C12N 9/50; C07H 21/04
(52) U.S. Cl. ............................ 435/219; 435/6; 435/68.1; 435/252.33; 435/320.1; 536/23.72
(58) Field of Search ............................... 435/6, 68.1, 219, 435/252.33, 320.1; 536/23.72

(56) References Cited

U.S. PATENT DOCUMENTS 4,652,552   3/1987   Kettner et al. .......................... 514/18

FOREIGN PATENT DOCUMENTS

| 0 048 455 | 3/1982 | (EP) . |
| 0 541 058 A1 | 5/1993 | (EP) . |
| 0 564 801 A1 | 10/1993 | (EP) . |

OTHER PUBLICATIONS

Belsham and Brangwyn, "A Region of the 5' Noncoding Region of Foot–and–Mouth Disease Virus RNA Directs Efficient Internal Initiation of Protein Synthesis within Cells: Involvement with the Role of L Protease in Translational Control," *J. Virol.* 64 5389–5395 (Nov. 1990).

Forss, S. et al., "Nucleotide Sequence and Genome Organization of Foot–and–Mouth Disease Virus," *Nucl. Acids Res.* 12:6587–6601 (1984).

Kräusslich, H.G. et al., "Poliovirus Proteinase 2A Induces Cleavage of Eucaryotic Initiation Factor 4F Polypeptide p220," *J. Virol.* 61:2711–2718 (Sep. 1987).

Piccone, M.E. et al., "Expression in *Escherichia coli* and Purification of Biologically Active L Proteinase of Foot–and–Mouth Disease Virus," *Chem. Abstr.* 122:264, Abstract No. 257357a (May 22, 1995).

English language version of International Search Report from corresponding International Appl. No. PCT/EP95/02742.

Allaire et al., "Picornaviral 3C cysteine proteinases have a fold similar to chymotrypsin–like serine proteinases," *Nature* 369:72–76 (1994).

Argos et al., "Similarity in gene organization and homology between proteins of animal picornaviruses and a plant comovirus suggest common ancestry of these virus families," *Nucleic Acids Res.* 12(18):7251–7267 (1984).

Bazan and Fletterick, "Viral cysteine proteases are homologous to the trypsin–like family of serine proteases: Structural and functional implications," *PNAS USA* 85:7872–7876 (1988).

Beck et al., Structure of the FMDV translation initiation site and of the structural proteins, *Nucleic. Acids. Res.* 11(22):7873–7885 (1983).

Bonneau and Sonenberg, "Proteolysis of the p220 Component of the Cap–Binding Protein Complex Is Not Sufficient for Complete Inhibition of Host Cell Protein Synthesis after Poliovirus Infection," *J. Virol.* 61(4):986–991 (1987).

Crawford and Goff, "A Deletion Mutation in the 5' Part of the pol Gene of Moloney Murine Leukemia Virus Blocks Proteolytic Processing of the gag and pol Polyproteins," *J. Virol.* 53(3):899–907 (1985).

Devaney et al., "Leader Protein of Foot–and–Mouth Disease Virus Is Required for Cleavage of the p220 Component of the Cap–Binding Protein Complex," *J. Virol.* 62(11):4407–4409 (1988).

Diez et al., "Unique Amino Acid Substitutions in the Capsid Proteins of Foot–and–Mouth Disease Virus from a Persistent Infection in Cell Culture," *J. Virol.* 64(11):5519–5528 (1990).

Duechler et al., "Evolutionary relationships within the human rhinovirus genus: Comparison of serotypes 89, 2, and 14," *PNAS USA* 84:2605–2609 (1987).

(List continued on next page.)

*Primary Examiner*—Ponnathapu Achutamurthy
*Assistant Examiner*—Richard Hutson
(74) *Attorney, Agent, or Firm*—Sterne, Kessler, Goldstein & Fox P.L.L.C.

(57) ABSTRACT

Methods of making and using Picornavirus L proteinase peptides (PLPPs) are provided, including, but not limited to, expression of DNA encoding all or a portion thereof, such as a Picornavirus L proteinase (PLP) and variants thereof, as well as methods for determining active sites and inhibitors of a PLP.

16 Claims, 8 Drawing Sheets

OTHER PUBLICATIONS

Geist et al., "In Vitro Activity of Zinc Salts against Human Rhinoviruses," *Antimicrob. Agents Chemother.* 31(4):622–624 (1987).

Gorbalenya et al., "Poliovirus–encoded proteinase 3C: a possible evolutionary link between cellular serine and cysteine proteinase families," *FEBS Lett.* 194(2):253–257 (1986).

Hämmerle et al., "Site–directed Mutagenesis of the Putative Catalytic Triad of Poliovirus 3C Proteinase," *J. Biol. Chem.* 266(9):5412–5416 (1991).

Hunkapiller and Hood, "Protein Sequence Analysis: Automated Microsequencing," *Science* 219:650–654,659 (1983).

Jackson et al., "The novel mechanism of initiation of picornavirus RNA translation," *TIBS* 15:477–483 (1990).

Joshi et al., "In Vitro Synthesis of Human Protein Synthesis Initiation Factor 4γ and Its Localization on 43 and 48 S Initiation Complexes," *J. Biol. Chem.* 269(3):2048–2055 (1994).

Katoh et al., "The effect of cerulenin on Moloney murine leukemia virus morphogenesis," *Virus Res.* 5:265–276 (1986).

Kirchweger et al., "Foot–and–Mouth Disease Virus Leader Proteinase: Purification of the Lb Form and Determination of Its Cleavage Site on eIF–4γ," *J. Virol.* 68(9):5677–5684 (1994).

Kitamura et al., "Structure and Expression of the Picornavirus Genome," *Ann. NY Acad. Sci.* 354:183–201 (1980).

Kleina and Grubman, "Antiviral Effects of a Thiol Protease Inhibitor on Foot–and–Mouth Disease Virus," *J. Virol.* 66(12):7168–7175 (1992).

Kohl et al., "Active human immunodeficiency virus protease is required for viral infectivity," *PNAS USA* 85:4686–4690 (1988).

Korant et al., "Viral Therapy: Prospects for Protease Inhibitors," *J. Cell. Biochem.* 32:91–95 (1986).

Lamphear et al., "Mapping the Cleavage Site in Protein Synthesis Initiation Factor eIF–4γ of the 2A Proteases from Human Coxsackievirus and Rhinovirus," *J. Biol. Chem.* 268(26):19200–19302 (1993).

Leong et al., "Human Rhinovirus–14 Protease 3C ($3C^{pro}$) Binds Specifically to the 5'–Noncoding Region of the Vira DNA," *J. Biol. Chem.* 268(34):25735–25739 (1993).

Liebig et al., "Purification of Two Picornaviral 2A Proteinases: Interaction with eIF–4γ and Influence on in Vitro Translation," *Biochemistry* 32(29):7581–7588 (1993).

Lloyd et al., "Relationship of p220 Cleavage during Picornavirus Infection to 2A Proteinase Sequencing," *J. Virol.* 62(11):4216–4223 (1988).

Medina et al., "The Two Species of the Foot–and–Mouth Disease Virus Leader Protein, Expressed Individually Exhibit the Same Activities," *Virology* 194:355–359 (1993).

Meek et al., "Human immunodeficiency virus 1 protease expressed in *E. coli* behaves as a dimeric aspartic protease," *PNAS USA* 86:1841–1845 (1989).

Perez and Carrasco, "Lack of Direct Correlation between p220 Cleavage and the Shut–Off of Host Translation after Poliovirus Infection," *Virology* 189:178–186 (1992).

Sangar et al., "All foot and mouth disease virus serotypes initiate protein synthesis at two separate AUG's," *Nucleic Acids Res.* 15(8):3305–3315 (1987).

Skern et al., "Human Rhinovirus 2: complete nucleotide sequence and proteolytic processing signals in the capsid protein region," *Nucleic Acids Res.* 13(6):2111–2126 (1985).

Skern et al., "Substrate Requirements of a Human Rhinoviral 2A Proteinase," *Virology* 181:46–54 (1991).

Sommergruber et al., "2A Proteinases of Coxsackie– and Rhinovirus Cleave Peptides Derived from eIF–4γ via a Common Recognition Motif," *Virology* 198:741–745 (1994).

Sommergruber et al., "Cleavage Specificity on Synthetic Peptide Substrates of Human Rhinovirus 2 Proteinase 2A," *J. Biol. Chem.* 267(31):22639–22644 (1992).

Strebel and Beck, "A Second Protease of Foot–and–Mouth Disease Virus," *J. Virol.* 58(3):893–899 (1986).

Studier et al., "Use of T7 RNA Polymerase to Direct Expression of Cloned Genes," *Methods Enzymol.* 185:60–89 (1990).

Wyckoff et al., "Eukaryotic initiation factor 3 is required for poliovirus 2A protease–induced cleavage of the p220 component of eukaryotic initiation factor 4F," *PNAS USA.* 87:9529–9533 (1990).

Wyckoff et al., "Relationship of Eukaryotic Initiation Factor 3 to Poliovirus–Induced p220 Cleavage Activity," *J. Virol.* 66(5):2943–2951 (1992).

Yan et al., "Amino Acid Sequence of the Human Protein Synthesis Initiation Factor eIF–4γ," *J. Biol. Chem.* 267(32):23226–23231 (1992).

Sambrook et al. (1989) Molecular Cloning: A Laboratory Manual. Cold Spring Harbor Laboratory Press. Cold Spring Harbor, New York.*

* cited by examiner

→ Lb
MetGluLeuThrLeuTyrAsnGlyGluLysLysThrPheTyrSerArgProAsnAsn
CCATGGAGTTAACACTGTACAACGGTGAGAAGAAGACCTTTTACTCCAGGCCCAACAACC    60

HisAspAsnCysTrpLeuAsnAlaIleLeuGlnLeuPheArgTyrValGluGluProPhe
ACGACAACTGCTGGTTGAACGCCATCCTCCAGTTGTTCAGGTACGTTGAAGAACCATTCT    120

PheAspTrpValTyrSerSerProGluAsnLeuThrLeuGluAlaIleLysGlnLeuGlu
TCGACTGGGTCTACAGTTCGCCTGAGAACCTCACGCTTGAAGCCATCAAGCAGTTGGAGG    180

AspLeuThrGlyLeuGluLeuHisGluGlyGlyProProAlaLeuValIleTrpAsnIle
ATCTCACAGGACTTGAACTGCATGAGGGTGGACCACCTGCTCTCGTGATCTGGAACATCA    240

LysHisLeuLeuHisThrGlyIleGlyThrAlaSerArgProSerGluValCysMetVal
AGCACTTGCTCCACACCGGCATCGGCACCGCCTCGCGACCCAGCGAGGTGTGCATGGTGG    300

AspGlyThrAspMetCysLeuAlaAspPheHisAlaGlyIlePheLeuLysGlyGlnGlu
ATGGTACGGACATGTGCTTGGCTGATTTCCATGCTGGCATTTTCCTTAAGGGGCAAGAAC    360

HisAlaValPheAlaCysValThrSerAsnGlyTrpTyrAlaIleAspAspGluAspPhe
ACGCTGTGTTTGCGTGTGTCACCTCCAACGGGTGGTACGCGATTGACGATGAGGACTTCT    420

TyrProTrpThrProAspProSerAspValLeuValPheValProTyrAspGlnGluPro
ACCCCTGGACGCCGGACCCGTCCGACGTTCTGGTGTTTGTCCCGTACGATCAAGAACCAC    480

→ VP4
LeuAsnGlyGluTrpLysAlaLysValGlnArgLysLeuLysGlyAlaGlyGlnSerSer
TCAACGGGGAATGGAAAGCCAAGGTTCAACGCAAGCTCAAAGGGGCTGGACAATCCAGTC    540

ProAlaThrGlySerGlnAsnGlnSerGlyAsnThrGlySerIleIleAsnAsnTyrTyr
CAGCGACCGGCTCGCAGAACCAATCTGGCAATACTGGCAGCATAATAAACAACTACTACA    600

MetGlnGlnTyrGlnAsnSerMetAspThrGlnLeuGlyAspAsnAlaIleSerGlyGly
TGCAGCAGTATCAAAACTCCATGGACACACAGCTTGGTGACAACGCAATCAGTGGAGGCT    660

→ VP2
SerAsnGluGlySerThrAspThrThrSerThrHisThrThrAsnThrGlnAsnAsnAsp
CTAACGAGGGCTCCACCGACACAACCTCCACCCACACAACCAACACCCAGAACAATGACT    720

TrpPheSerLysLeuAlaSerSerAlaPheSerGlyLeuPheGlyAlaLeuLeuAlaAsp
GGTTCTCCAAACTTGCCAGCTCTGCTTTCAGCGGTCTTTTCGGCGCTCTTCTCGCCGACA    780

LysLysThrGluGluThrThrLeuLeuGluAspArgIleLeuThrThrArgAsnGlyHis
AGAAGACAGAGGAGACCACTCTCCTCGAAGACCGCATCCTCACCACCCGTAACGGCCACA    840

ThrThrSerThrThrGlnSerSerValGlyValThrTyrGlyTyrAlaThrAlaGluAsp
CCACGTCGACAACCCAGTCAAGCGTTGGAGTCACATACGGGTACGCAACAGCTGAAGATT    900

PheValSerGlyProAsnThrSerGlyLeuGluThrArgValValGlnAlaGluArgPhe
TTGTGAGCGGACCGAACACTTCCGGTCTCGAAACCAGAGTTGTGCAGGCAGAACGGTTTT    960

PheLysThrHisLeuPheAspTrpValThrSerAspSerPheGlyArg******
TCAAAACCCACCTCTTCGACTGGGTCACCAGTGACTCATTCGGACGTTGATAAGGATCC    1019

FIG.1

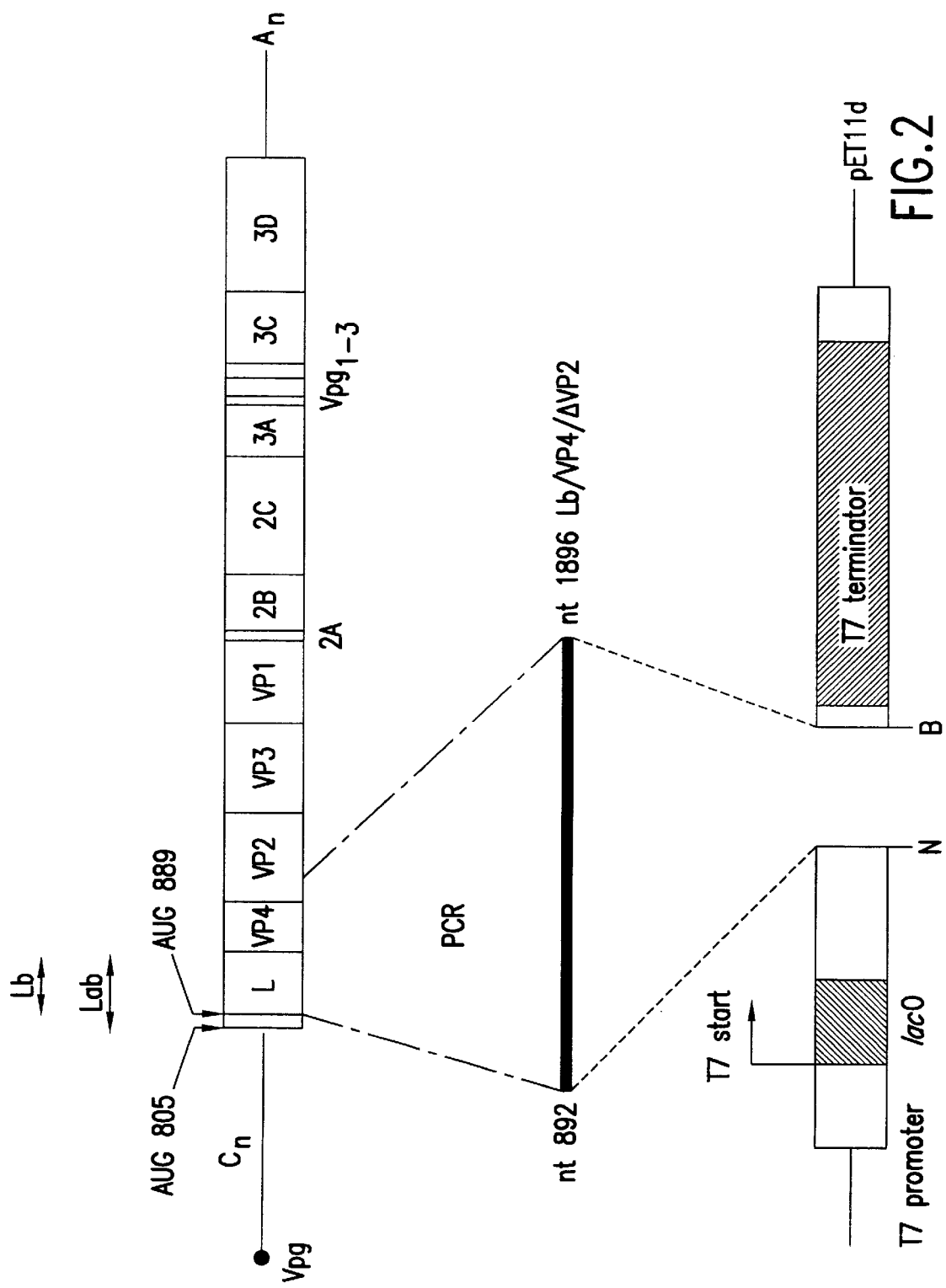

FMDV

```
                    L           VP4
                       206
             199 AKVQRKLK    GAGQSSPA 215
                        ↑
                       Lb        2A
                        ↓         ↓
          472 TPSFANLG     RPALSSR     GPPRGGPG 494
                     |            |
                    479          486
``` eIF-4γ ├──┬────┬────┬────┬────┬────┬────┬──┤
        200  400  600  800 1000 1200 1400
              ↑                      ↑
         Anti-peptide #7        Anti-peptide #6

PICORNAVIRUS I PROTEINASE AND METHODS OF MAKING AND USING THEREOF

This application is a continuation of application Ser. No. 08/279,152, filed Jul. 22, 1994, now abandoned.

BACKGROUND OF THE INVENTION

1. Field of the Invention

The present invention is in the field of virology and molecular biology. More specifically the present invention relates to methods of making and using Picornavirus L proteinase peptides (PLPPs), including, but not limited to, expression of DNA encoding all or portions thereof, such as for Picornavirus L proteinase (PLP) and variants thereof, as well as methods for determining active sites and inhibitors of a PLP.

2. Related Background Art

Many viruses manipulate the cellular machinery of the host cell to their own advantage (Watson, J. et al. 1987. *Molecular Biology of the Gene*, Fourth Edition, Vol. II. The Benjamin/Cummings Publishing Company, Inc., Menlo Park, Calif.). One of the strategies of the single-stranded RNA Picornaviruses is to modify the translational machinery (Rueckert, R. R., in *Field's Virology*, Second Edition, B. N. Fields et al., eds., Raven Press, New York (1990), Vol. 1, pp. 507–548). Infection by the Picornaviruses, rhino-, entero- and aphthoviruses, leads to a reduction in the translation of capped host cell mRNAs. However, translation of viral RNAs is not affected as viral RNAs are not capped and translation of such RNAs is initiated internally (Sonenberg, N., *Current Top. Microbiol. Immunol.* 161:23–47 (1990)).

The mechanism of this reduction is thought to occur through proteolytic cleavage of the eIF-4γ polypeptide, which leads to an inability of the host cell to translate capped mRNAs (Lloyd, R. E. et al., *J. Virol.* 61:2480–2488 (1987)). eIF-4γ is a member of the eIF-4 group of translational initiation factors (the others are eIF-4A, eIF-4B, and eIF-4E) which collectively recognize the capped 5'-terminus of mRNA, unwind mRNA secondary structure, and permit the scanning by the 40S ribosomal subunit for the initiation codon (Merrick, W. C., *Microbiol. Reviews* 56:291–315 (1992); Rhoads, R. E., *J. Biol. Chem.* 266:3017–3020 (1993)). eIF-4γ is a polypeptide of calculated molecular mass 154 kDa but with an apparent mobility on SDS-PAGE corresponding to 220 kDa (eIF-4γ was previously designated p220). The protein is always found as a collection of three to four bands on SDS-PAGE, but neither the heterogeneity nor aberrant mobility are understood (Yan R. et al., *J. Biol. Chem.* 267:23226–23231 (1992)). The role of eIF-4γ during initiation has not been elucidated, but recent observations on the distribution of eIF-4γ polypeptides among the various initiation complexes (Joshi, B. et al. *J. Biol. Chem.* 269:2048–2055 (1994)) suggest the following model: eIF-4E first binds to the mRNA cap as a free polypeptide; it then forms a complex with eIF-4γ which is already present on the 40S ribosomal subunit, thereby assembling the machinery which carries out unwinding of secondary structure. This, proteolytic cleavage of eIF-4γ may separate the eIF-4E binding domain from the ribosome-binding domain and prevent the cap-dependent recruitment of mRNA to the ribosome.

The initiation of uncapped picornaviral RNAs can take place in the presence of proteolytically cleaved eIF-4γ as it occurs internally on a 450 nucleotide segment of the 5' UTR, known as the internal ribosome entry segment (IRES). This event takes place in all picornaviruses, although there may be differences in the mechanisms as there is little similarity between the IRES elements of rhino- and enteroviruses and those of cardio- and aphthovirus and that of Hepatitis A virus (Jackson, R. et al., *Trends in Biochem. Sci.* 15:477–483 (1990)).

However, the relevance of the eIF-4γ cleavage to the host cell shut-off is still controversial. Firstly, several reports claim that cleavage of eIF-4γ alone is not sufficient to elicit the host cell shut-off (e.g., Bonneau & Sonenberg, *J. Virol.* 61:986–991 (1987); Perez & Carrasco, *Virology* 189:178–186 (1992)). Secondly, the proteolytical activity carrying out the eIF-4γ cleavage has been the subject of dispute. For rhino- and enteroviruses, a mechanism involving the activation of a cellular proteinase by the 2A proteinase had been proposed; cleavage of the eIF-4γ molecule was then performed by the former (Kräusslich, H.-G. et al., *J. Virol.* 61:2711–2718 (1987); Wyckoff, E. E. et al., *Proc. Natl. Acad. Sci. USA*. 87:9529–9533 (1990); Wyckoff, E. E. et al., *J. Virol.* 66:2943–2951 (1992)). However, recent experiments with purified recombinant 2A proteinases have contradicted this hypothesis. The findings that the 2A proteinase cleavage sequence on eIF-4γ is similar to the preferred cleavage specificity of the proteinases and the ability of these 2A proteinases to cleave a peptide of this sequence show that the 2A proteinases do indeed cleave eIF-4γ directly (Lamphear, B. J. et al., *J. Biol. Chem.* 268:19200–19203 (1993); Sommergruber, W. H., et al., *Virology* 198:741–745 (1994)).

The situation in the Picornavirus aphthoviruses (e.g., Foot-and-Mouth Disease Virus, FMDV) is different; eIF-4γ cleavage is mediated by the viral-encoded leader L proteinase and not by the 2A proteinase (Devaney, M. A. et al., *J. Virol.* 62:4407–4409 (1988); Lloyd, R. E. et al., *J. Virol.* 62:4216–4223 (1988)). However, the nature of the in vivo cleavage products is not clear; one report (Medina, M. E. et al., *Virology* 194:355–359 (1993)) states that they are identical to those found during poliovirus infection, whereas two reports describe different products (Lloyd, R. E. et al., *J. Virol.* 62:4216–4223 (1988); Kleina & Grubman, *J. Virol.* 66:7168–7175 (1992)). The site of cleavage of the FMDV L proteinase on eIF-4γ has not yet been identified. It is also not known whether cleavage is a direct event.

The nature of the L proteinase itself is also poorly understood. Amino acid sequence comparisons have indicated a similarity to papain-like thiol-proteinases (Gorbalenya, A. E. et al., *FEBS Lett.* 288:201–205 (1991)); the inhibition of the enzyme by E64, a specific inhibitor of this class of proteinases supports this suggestion (Kleina & Grubman, *J. Virol.* 66:7168–7175 (1992)). Although the 2A proteinases of rhino- and enteroviruses are also thiol-proteinases, they are not related to papain; instead, they have a high similarity to serine proteinases, such as chymotrypsin and α-lytic proteinase (Argos, P. et al., *Nucleic Acids Res.* 12:7251–7267 (1984); Bazan & Fletterick, *Proc. Natl. Acad. Sci. USA* 85:7872–7876 (1988); Gorbalenya, A. E. et al., *FEBS Lett.* 194:253–257 (1986)). In addition, the FMDV L proteinase and the 2A proteinases are located at different positions on the viral polyprotein. The L proteinase is encoded at the extreme N-terminus of the polyprotein, with cleavage taking place between the C-terminus of the L proteinase and the N-terminus of VP4, whilst rhino- and enterovirus 2A proteinases cleave between the C-terminus of VP1 and their own N-terminus. Furthermore, two forms of the L proteinase (Lab and Lb; see FIG. 1) are found in the infected cell, as translation of the FMDV RNA can begin at one of two AUG codons (Sangar, D. V. et al., *Nucleic Acids*

Res. 15:3305–3315 (1987)). Both forms exhibit the same enzymatic activities (Medina, M. E. et al., *Virology* 194:355–359 (1993)).

The expression of viral proteinases has generally proved to be difficult for two reasons. Firstly, most viral proteinases (including the HIV proteinase, rhinovirus 2A proteinase and enteroviral 2A proteinase) are toxic for the *E. coli cell*. Secondly, these proteins are insoluble at high levels of expression. Both problems were encountered with the Lb proteinase. Previously the modification of the bacterial T7 RNA polymerase expression system has been used with some success for HRV2 and CVB4 2A proteinase expression (Liebig, H.-D. et al., *Biochemistry* 32:7581–7588 (1993)).

The general importance of inhibiting virally coded proteinase has been moved back into the spotlight of possible anti viral therapeutic approaches not least by studies with the proteinase of human immunodeficiency virus 1 (HIV I). By deletion and point mutations in the proteinase region of this kind of retrovirus, it has been possible to recognize the essential role of the proteinase in the maturation of this type of virus (Katoh, I. et al., *Virol.* 145:280–292 (1985); Kohl, N. E. et al., *Proc. Natl. Acad. Sci. USA* 85:4686–4690 (1988); Crowford, S. and Goff, S. P., *J. Virol.* 53:899–907 (1985)). It has also been shown, by X-ray structural analysis and molecular biological studies, that the proteinase of HIV I belongs to the Asp-type, can process itself on the precursor protein (in recombinant prokaryotic systems as well), is capable of cleaving "in trans" specific peptides and occurs as an active proteinase in a homodimeric form (Navia, M. A. et al., loc. cit. (1989); Meek, T. D. et al., loc. cit. (1989); Katoh, I. et al., loc. cit. (1985)). In view of the fact that the proteinase of HIV I occurs as a dimer in its active form, Wlodawer and colleagues also proposed the development of specific dimerization inhibitors (Wlodawer, A. et al., *Science* 245:616–621 (1989)). The development of highly specific competitive inhibitors against the proteinase of HIV I on the basis of modified peptide substrates was described only recently by Tomasselli and colleagues (Tomasselli, A. G. et al., *Biochem.* 29:264–269 (1990)). It had been known for even longer that a fungicidal antibiotic, cerulenin, has an anti retroviral activity against Rous Sarcoma Virus and Murine Leukemia Virus (Goldfine, H. et al., *Biochem. Biophys. Acad.* 512:229–240 (1978); Katoh, I. et al., *Virus Res.* 5:265–276 (1986)). In the case of HIV I, it was possible to make a connection between the inhibitory effect of cerulenin and the inhibition in the proteolytic processing of the polyprotein of HIV I (Pal, R. et al., *Proc. Natl. Acad. Sci.* 85:9283–9286 (1988)). Starting from this fact, Blumenstein and colleagues were able to develop specific inhibitors against proteinase HIV I on the basis of synthetic non-peptide inhibitors. In other words, they were able to trace the inhibitory effect of cerulenin to the interaction of the electrophilic epoxide group with nucleophilic regions of the proteinase. Moreover, as a result of the development of synthetic derivatives, the original toxicity of cerulenin has been reduced (Blumenstein, J. J. et al., *Biochem. Biophys. Res. Commun.* 163:980–987 (1989)).

Also in the picornaviral system, some organic or inorganic compounds, as well as peptide derivatives and proteins are now known which have an inhibitory effect on the proteolytic processing of these viruses. The effect of these substances is based on the direct interaction with the proteinases (Kettner, C. A. et al., U.S. Pat. No. : 4,652,552 (1987); Korant, B. D. et al., *J. Cell. Biochem.* 32:91–95 (1986) and/or on the indirect route of interaction with substrates of these proteinases (Geist, F. C. et al., *Antimicrob. Agents Chemother.* 31:622–624 (1987); Perrin, D. D. and Stünzi, H., *Viral Chemotherapy* 1:288–189 (1984)). The problem with the majority of these substances is the relatively high concentration required for inhibition and the toxicity of these compounds, which is considerable with some of them. Thus, it is highly desirable to develop a systematic method for the identification of new picornaviral proteinase inhibitors which could be used, e.g., in the treatment of picornavirus infections.

Citation of documents herein is not intended as an admission that any of the documents cited herein is pertinent prior art, or an admission that the cited documents is considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

The present invention is intended to overcome one or more deficiencies of the related background art.

The present invention provides a DNA molecule comprising a DNA expression vector, and a DNA segment encoding a picornavirus L proteinase or variant thereof, wherein the variant arises from mutation, deletion or insertion and the molecule is capable of expressing the picornavirus L proteinase or variant thereof.

The present invention further provides a vector and/or host that contains the above-described DNA molecule which is capable of expressing the picornavirus as a variant in recoverable amounts.

The present invention also provides a method of producing and/or purifying a picornavirus L proteinase, or variant thereof, resulting in a good yield of active soluble L proteinase.

The present invention additionally provides a method for the analysis of the cleavage of eukaryotic elongation factor eIF-4γ or variant thereof by a picornavirus L proteinase or variant thereof.

The present invention also provides a method for the identification of inhibitory substances of picornavirus L proteinases.

The present invention further provides a method for the identification of inhibitory substances of FMDV L proteinase catalyzed site specific cleavage of eIF-4γ, or a variant thereof.

The present invention also provides test systems for identification of inhibitory substances of picornavirus L proteinases.

Other aspects, embodiments and uses of the present invention will be apparent to skilled practitioners from the following detailed description and examples relating to the present invention. The present invention is herein after described in detail.

BRIEF DESCRIPTION OF THE FIGURES

FIG. 1. The nucleotide and derived amino acid sequences of the FMDV expression block of pET8c/FMDV Lb and pET11d/FMDV Lb are shown. The NcoI (beginning) and BamHI (end) restriction sites that constitute the transition sites with the plasmid sequences are also shown. Nucleotide 6 of the sequence corresponds to nucleotide 892 of the FMDV sequence, and nucleotide 1009 corresponds to nucleotide 1895 of the FMDV sequence (SEQ ID NO:1). The two in-phase stop codons are represented by asterisks.

FIG. 2. The expression block of plasmid pET11d/Lb. The FMDV genome is shown diagrammatically; the lines indicate non-coding regions and the boxes the positions of the mature viral proteins. The two initiating AUG codons at 805 and 889 which give rise to the two forms of the L proteinase, Lab and Lb, are indicated. Nucleotides 892 to 1896 were amplified by PCR and cloned into pET11d which had been cleaved by NcoI (N) and BamHI (B), followed by a fill-in reaction with the Klenow fragment of *E. coli* DNA polymerase I. Translation of the FMDV sequences begins in phase with the AUG codon of the S10 T7 protein at the NcoI site.

Lane 1: crude cell extract (fraction 1).

Lane 2: ammonium sulphate precipitation (fraction 2).

Lane 3: Pooled ion-exchange chromatography (mono-Q®) fractions; (fraction 3)

Lane 4: Pooled and concentrated gel filtration (superdex®) fractions (fraction 4).

Figure 4:
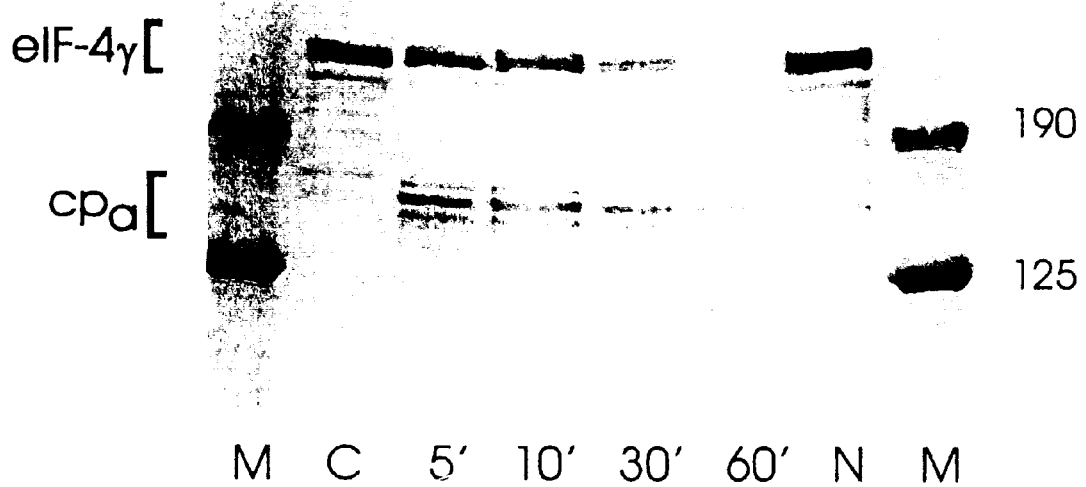

FIG. 4. In vitro cleavage of eIF-4γ in IBRS-2 cell extracts. IBRS-2 cytoplasmic cell extract was incubated with 0.3 μg Lb proteinase as described in example 4. The reaction was stopped at the times indicated by the addition of Laemmli sample buffer and the proteins were separated by SDS-PAGE on a gel containing 6% acrylamide. The gel was blotted onto nitrocellulose and probed with the rabbit anti-eIF-4γ peptide 7 antiserum. Key: C, IBRS-2 cytoplasmic extract; M, marker proteins; N, IBRS-2 cytoplasmic extract incubated for 60 min at 30° C. in the absence of Lb proteinase; $cp_a$, N-terminal cleavage products. The numbers on the right indicate apparent molecular sizes (in kDa).

Figure 5A:
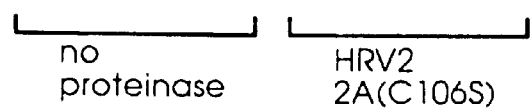
Figure 5B:
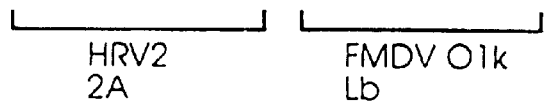

FIGS. 5A and 5B. In vitro cleavage of eIF-4γ in HeLa cell extracts by FMDV Lb proteinase and HRV2 2A proteinase. HeLa cytoplasmic cell extract (7.5 μg) was incubated with 1 μg of the indicated proteinases as described in example 5, the reactions stopped by the addition of Laemmli sample buffer and analyzed by immunoblotting as described in FIG. 4. Key; $cp_a$, N-terminal cleavage products; M, marker proteins pre-stained with Coomassie blue.

Figure 6A:
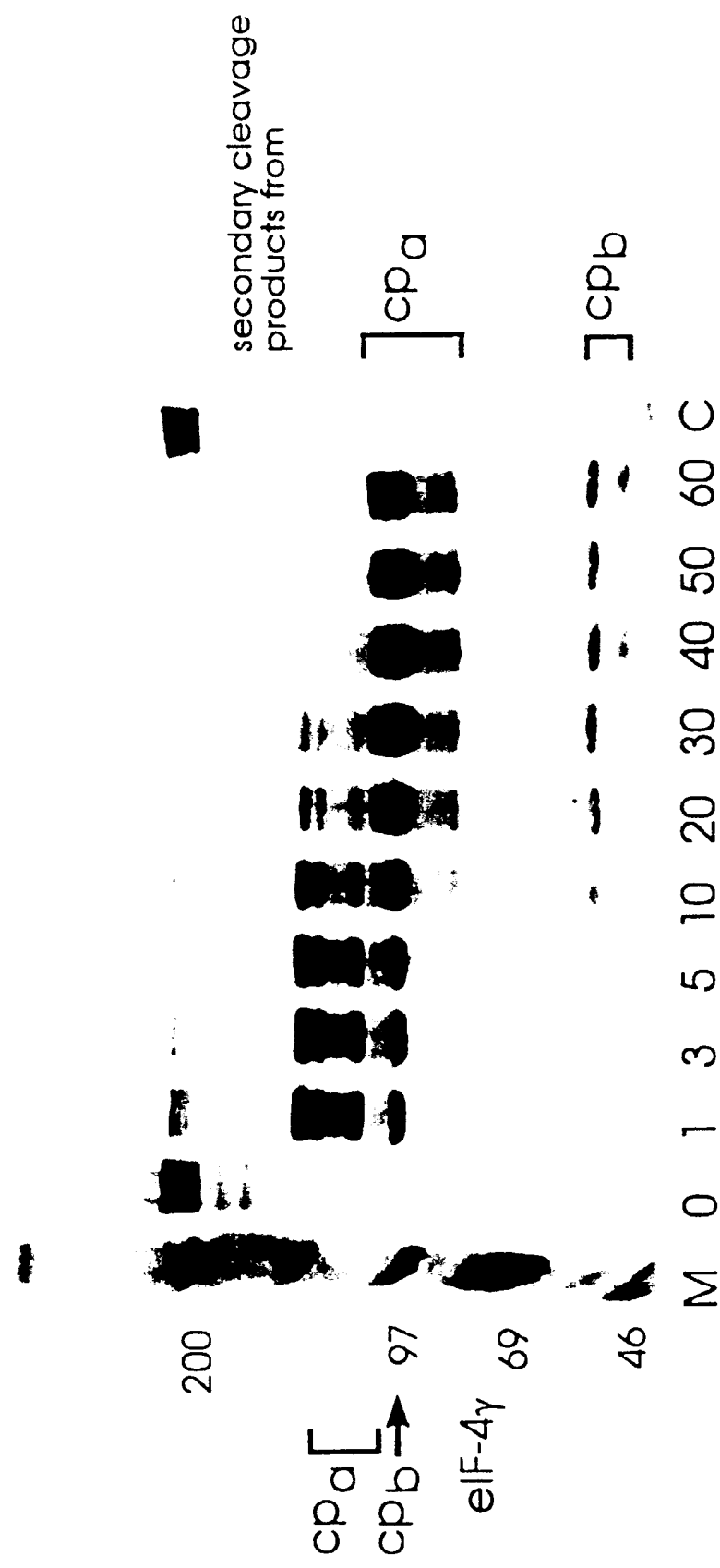
Figure 6B:
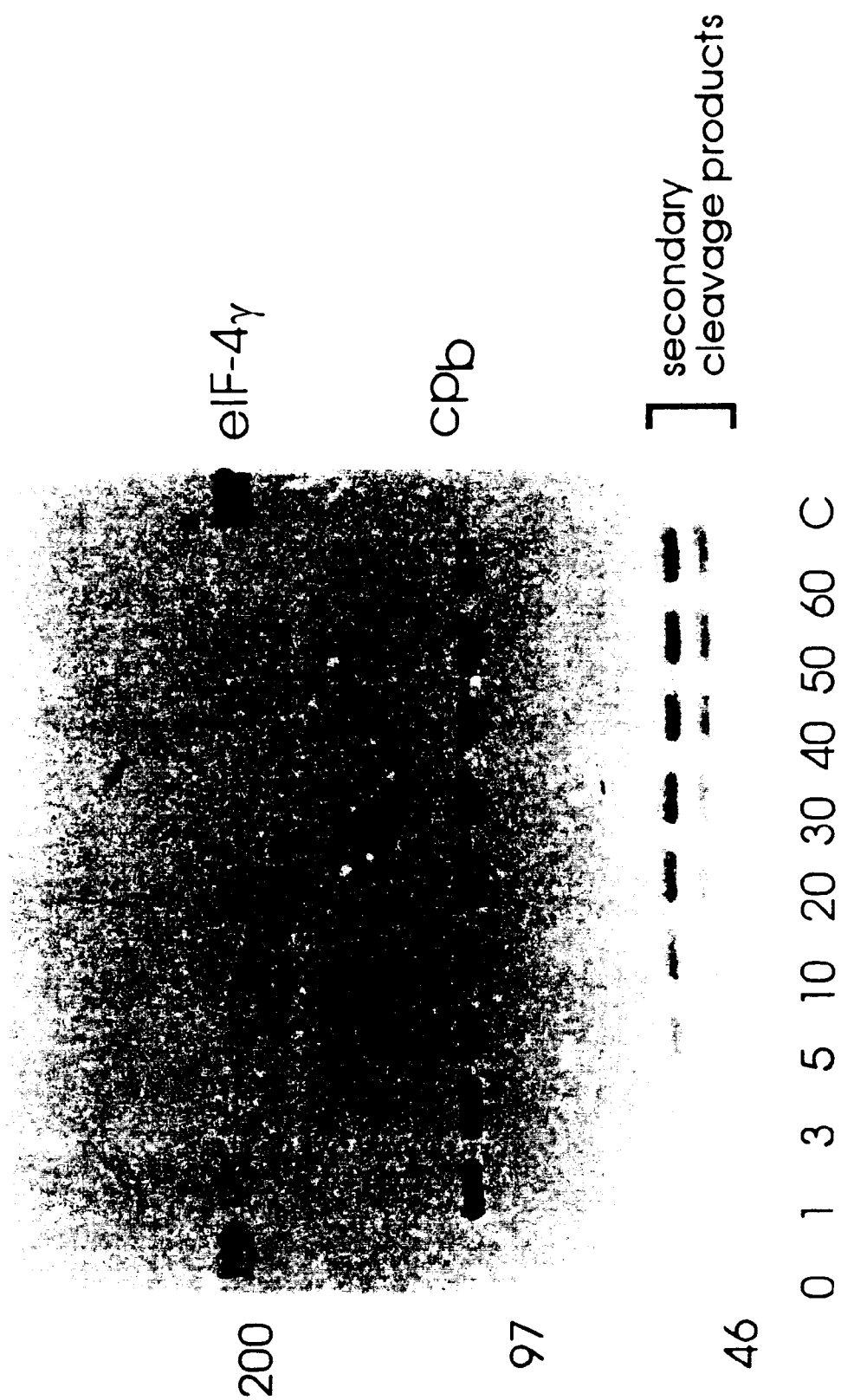

FIGS. 6A and 6B. Time course of eIF-4γ cleavage by FMDV Lb proteinase. Reactions were performed as described in example 6. Aliquots were removed at the times indicated and analyzed by SDS-PAGE on an 6.5% polyacrylamide gel followed either by silver staining (panel A) or immunoblotting with rabbit anti-eIF-4γ peptide 6 antiserum, an antiserum against a synthetic peptide from the C-terminus of eIF-4γ (panel B). Lane C shows eIF-4γ incubated for 60 min in the absence of Lb proteinase. The numbers on the left indicate apparent molecular sizes (in kDa); $cp_a$ and $CP_b$ indicate the positions of N-terminal and C-terminal fragments of eIF-4γ, respectively.

FIG. 7. Diagrammatic representation of the eIF-4γ molecule. The line represents the primary sequence of the rabbit eIF-4γ molecule; the amino acids 472 to 494 are shown and the positions of the picornaviral proteinase cleavage sites are marked. The cleavage site of the L proteinase on the FMDV viral polyprotein between the L proteinase C-terminus and the N-terminus of VP4 (Palmenberg, A. C., In: Molecular Aspects of Picornavirus Infection and Detection, Eds: B. L. Semler and E. Ehrenfeld. American Society for Microbiology, Washington, D.C., pp. 221–242 (1989)) is shown for comparison. The positions of the peptides used to make the rabbit anti-eIF-4γ peptide 6 and 7 antisera are also shown.

Figure 8:
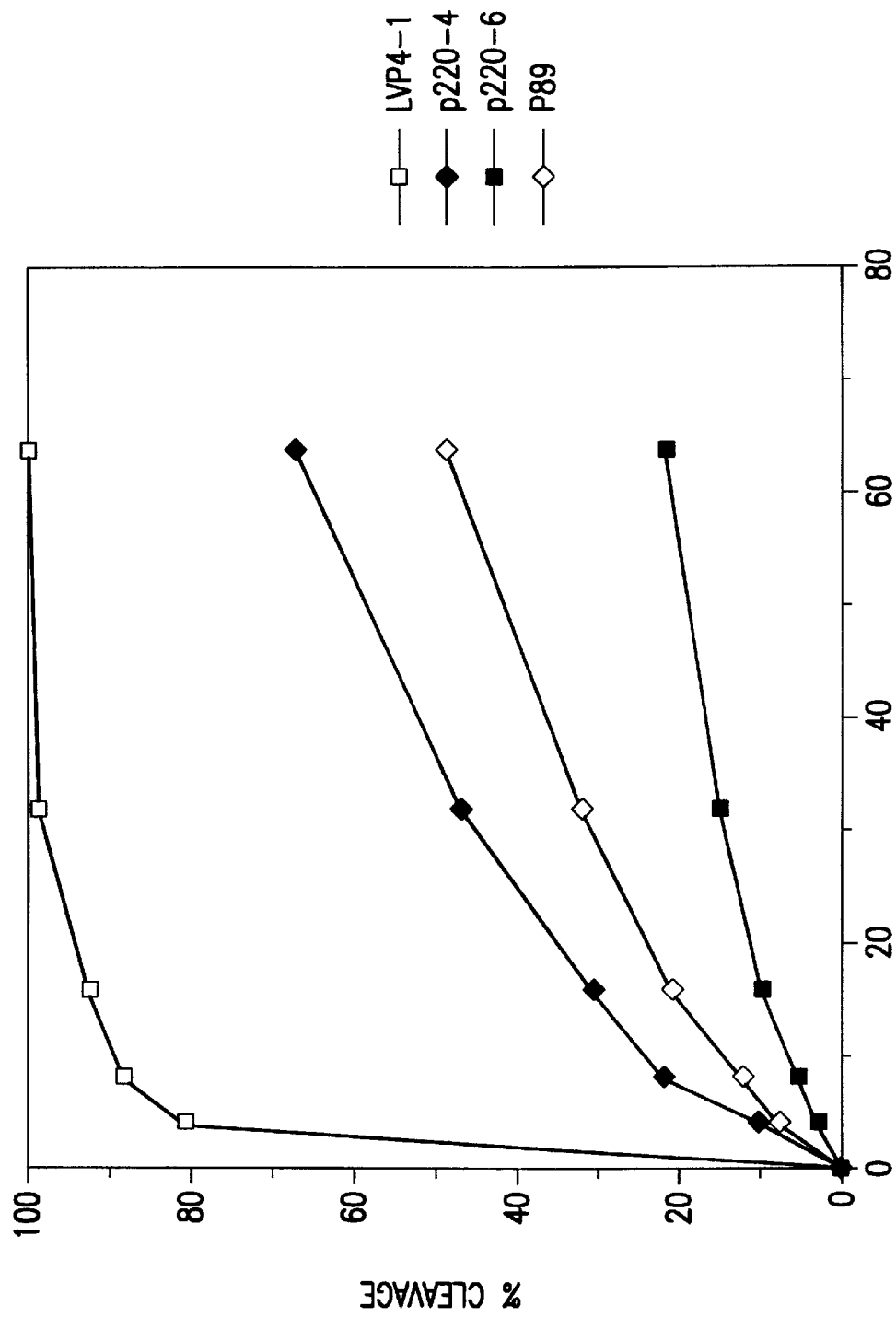

FIG. 8. Time course of the cleavage of synthetic peptide substrates by Lb proteinase. Synthetic peptides P89, p220-4, p220-6, and LVP4-1 (Table 3) were incubated at a concentration of 100 μM in 50 mM Tris/HCl (pH 8.0), 150 mM NaCl, 1 mM EDTA, and 5 mM DTT in the presence of 10 μg/ml Lb proteinase at 37° C. for 4, 8, 16, 32 or 64 min and the reaction products analyzed as described in example 8.

DETAILED DESCRIPTION OF THE PREFERRED EMBODIMENTS

One aim of the present invention is to express a picornavirus L proteinase (PLP), or variant thereof, in a reproducible and good yield as a mature, active proteinase.

The expression of viral proteinases has generally proved to be difficult for two reasons. Firstly, most (including the HIV proteinase, rhino- and enteroviral 2A proteinases) are toxic for the *E. coli* cell; secondly, these proteins are insoluble at high levels of expression. Both problems were encountered with picornavirus L proteinase; they could only be solved with considerable efforts using the experience gained in expressing the 2A proteinase of HRV2. However, the L proteinases, members of a different group of proteinases than the 2A proteinase (see above) appeared to be more toxic than the 2A proteinases, as even the small amounts of non-repressed L proteinase expression present using e.g., the vector pET8c in the *E. coli* BL21(DE3)LysE strain led to rapid loss of expression.

Since the Lb proteinase appeared to be more toxic than these 2A proteinases, as even the small amounts of non-repressed expression present using the vector pET8c in the *E. coli* BL21(DE3)LysE strain led to rapid loss of expression.

To enable a thorough characterization of a picornavirus L proteinase, such as FMDV L proteinase, and to investigate its interaction with eIF-4γ, it was therefore necessary to establish an efficient expression system from which pure mature soluble L proteinase can be prepared. Due to the different biology of FMDV and the different proteolytic mechanism of the L protein, a different expression strategy of L proteinase was necessary in order to ensure highly reproducible expression of L proteinase, resulting in good yield of mature L proteinase.

The course of picornavirus infection is critically dependent on the viral proteinases. These very enzymes constitute an ideal target for chemotherapeutic intervention, e.g. the viral L proteinase. The chemotherapeutic point of attack is the inhibition of enzymatic activity by specific inhibitors. Picornavirus L Proteinases (PLP) Peptide (PLPP).

A picornavirus proteinase peptide (PLPP), according to the present invention, can refer to any subset of a picornavirus L proteinase (PLP) having PLP activity. A peptide fragment according to the present invention can be prepared by proteolytic digestion of the intact molecule or a fragment thereof, by chemical peptide synthesis methods well-known in the art, by recombinant DNA methods discussed in more detail below, and/or by any other method capable of producing a PLPP and having a conformation similar to an active portion of PLP and having L proteinase activity, according to known L proteinase activity as screening assays, e.g., as described herein. The minimum peptide sequence to have activity is based on the smallest unit containing or comprising a particular region, consensus sequence, or repeating unit thereof of a PLP having L proteinase activity.

Accordingly, a PLPP of the present invention alternatively includes polypeptides having a portion of a PLP amino acid sequence which substantially corresponds to at least one 50 to 400 amino acid fragment and/or consensus sequence of a known Picornavirus L proteinase or group of PLPs, wherein the PLPP has homology of at least 80%, such as 80–99% homology, or any range or value therein, while maintaining L proteinase biological activity, wherein a PLPP of the present invention is not naturally occurring or is naturally occurring but is in a purified or isolated form which does not occur in nature. Preferably, a PLPP of the present invention substantially corresponds to a L proteinase domain of a picornavirus or group of Picornaviruses as a consensus sequence, such as an FMDV L proteinase, such as proteinase Lb.

Percent homology may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *ATLAS OF PROTEIN SEQUENCE AND STRUCTURE*, National Biomedical Research Foundation, pp. 353–358 (1979); (2) a penalty of 3.0 for each gap and an additional 0.10 penalty for each symbol in each gap; and (3) no penalty for end gaps.

In a preferred embodiment, the peptide of the present invention corresponds to an active portion of SEQ ID NO:2.

A peptide of at least about 50–335 amino acids (or any range or value therein) that has the basic structure of the active portion of a PLP can, in one embodiment, be characterized as having 80–99% homology (or any range or value therein) to the above PLP sequences, which peptide can have PLP activity and is contemplated within the scope of the present invention. Thus, one of ordinary skill in the art, given the teachings and guidance presented in the present specification, will know how to substitute other amino acid residues in other positions of a PLP to obtain a PLPP, including substituted, deletional or insertional variants.

A PLPP of the present invention also includes a variant wherein at least one amino acid residue in the polypeptide has been conservatively replaced, inserted or deleted by at least one different amino acid.

An amino acid or nucleic acid sequence of a PLPP of the present invention is said to "substantially correspond" to another amino acid or nucleic acid sequence respectively, if the sequence of amino acids or nucleic acid in both molecules provides polypeptides having biological activity that is substantially similar, qualitatively or quantitatively, to the corresponding fragment of at least one PLP domain having PLP activity. Such "substantially corresponding" PLPP sequences include conservative amino acid or nucleotide substitutions, or degenerate nucleotide codon substitutions wherein individual amino acid or nucleotide substitutions are well known in the art.

Accordingly, PLPPs of the present invention, or nucleic acid encoding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins. Structure and Molecular Properties*, W. H. Freeman & Co., San Francisco, 1983, which are hereby incorporated by reference. For a presentation of nucleotide sequence substitutions, such as codon preferences, see Ausubel et al., eds, *Current Protocols in Molecular Biology*, Greene Publishing Assoc., New York, N.Y. (1987, 1988, 1989, 1990, 1991, 1992, 1993, 1994) at §§A.1.1–A.1.24, and Sambrook et al, *Molecular Cloning. A Laboratory Manual*, Second Edition, Cold Spring Harbor Press, Cold Spring Harbor, N.Y. (1989), at Appendices C and D.

Amino Acid Substitutions of Native PLP for a PLPP.

Conservative substitutions of a PLPP of the present invention includes a variant wherein at least one amino acid residue in the polypeptide has been conservatively replaced, inserted or deleted by at least one different amino acid.

Such substitutions preferably are made in accordance with the following list as presented in Table 1, which substitutions can be determined by routine experimentation to provide modified structural and functional properties of a synthesized polypeptide molecule, while maintaining PLP biological activity, as determined by known PLP activity assays. In the context of the present invention, the term PLPP or "substantially corresponding to" includes such substitutions.

TABLE 1

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Accordingly, based on the above examples of specific substitutions, alternative substitutions can be made by routine experimentation, to provide alternative PLPPs of the present invention, e.g., by making one or more conservative substitutions of PLP fragments which provide PLP activity.

Alternatively, another group of substitutions of PLPPs of the present invention are those in which at least one amino acid residue in the protein molecule has been removed and a different residue inserted in its place according to the following Table 2. The types of substitutions which can be made in the protein or peptide molecule of the present invention can be based on analysis of the frequencies of amino acid changes between a homologous protein of different species, such as those presented in Table 1–2 of Schulz et al., infra. Based on such an analysis, alternative conservative substitutions are defined herein as exchanges within one of the following five groups:

TABLE 2

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than $\alpha$-helical. Pro, because of its unusual geometry, tightly constrains the chain. It generally tends to promote $\beta$-turn-like structures, although in some cases Cys can be capable of participating in disulfide bond formation which is important in protein folding. Note that Schulz et al. would merge Groups 1 and 2, above. Note also that Tyr, because of its hydrogen bonding potential, has significant kinship with Ser, and Thr, etc.

Conservative amino acid substitutions, included in the term "substantially corresponding" or "corresponding", according to the present invention, e.g., as presented above, are well known in the art and would be expected to maintain biological and structural properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. $\alpha$-helix or $\beta$-sheet, as well as changes in physiological activity, e.g. in receptor binding assays.

However, when the exact effect of the substitution, deletion, or insertion is to be confirmed, one skilled in the art will appreciate that the effect of the substitution or substitutions will be evaluated by routine PLP activity screening assays, either immunoassays or bioassays, to confirm biological activity, such as, but not limited to, L proteinase.

Amino acid sequence insertions as included in PLPP variant can also include amino and/or carboxyl-terminal fusions of from one residue to polypeptides of essentially unrestricted length, as well as intrasequence insertions of single or multiple amino acid residues. Intrasequence insertions can range generally from about 1 to 10 residues, more preferably 1 to 5. An example of a terminal insertion includes a fusion of a signal sequence, whether heterologous or homologous to the host cell, to a PLPP to facilitate secretion from recombinant bacterial hosts.

One additional group of variants according to the present invention is those in which at least one amino acid residue in the peptide molecule, and preferably, only one, has been removed and a different residue inserted in its place.

For a detailed description of protein chemistry and structure, see Schulz et al., *Principles of Protein Structure*, Springer-Verlag, New York, 1978; Ausubel, infra, which are hereby incorporated by reference.

Most deletions and insertions, and substitutions of PLPPs according to the present invention are those which maintain or improve the L proteinase characteristics of the peptide molecule. However, when it is difficult to predict the exact effect of the substitution, deletion, or insertion in advance of doing so, one skilled in the art will appreciate that the effect will be evaluated by routine screening assays. For example, a variant made by site-specific mutagenesis of the peptide molecule-encoding nucleic acid and expression of the variant PLPP in cell culture or, alternatively, by chemical synthesis, can be tested for L proteinase activity (e.g., as is known or as described herein). The activity of the cell lysate or purified peptide variant can be screened in a suitable screening assay for the desired characteristic, for example L proteinase activity in any of the several assays.

Modifications of peptide properties, such as redox or thermal stability, hydrophobicity, susceptibility to proteolytic degradation or the tendency to aggregate with carriers or into multimers, can also be assayed by methods well known to the ordinarily skilled artisan.

Also included in the scope of the invention are salts of the PLPPs of the invention. As used herein, the term "salts" refers to both salts of carboxyl groups and to acid addition salts of amino groups of the protein or peptide molecule.

Amino acid sequence variants of a PLPP of the present invention can also be prepared by mutations in the DNA. Such variants include, for example, deletions from, or insertions or substitutions of, residues within the amino acid sequence. Any combination of deletion, insertion, and substitution can also be made to arrive at the final construct, provided that the final construct possesses some L proteinase activity. Preferably improved L proteinase activity is found over that of the non-variant peptide. Obviously, mutations that will be made in the DNA encoding the variant must not place the sequence out of reading frame and preferably will not create complementary regions that could produce secondary mRNA structure (see, e.g., EP Patent Application Publication No. 75,444; Ausubel, infra; Sambrook, infra).

At the genetic level, these variants ordinarily are prepared by site-directed mutagenesis of nucleotides in the DNA encoding a PLPP, thereby producing DNA encoding the variant, and thereafter expressing the DNA in recombinant cell culture. The variants typically exhibit the same qualitative biological activity as the naturally occurring PLP (see, e.g., Ausubel, infra; Sambrook, infra).

Knowledge of the three-dimensional structures of proteins is crucial in understanding how they function. The three-dimensional structures of more than 400 proteins are currently available in the protein structure database (in contrast to around 200,000 known protein and peptide sequences in sequence databases, e.g., Genbank, Chemical Abstracts REGISTRY, etc.). Analysis of these structures shows that they fall into recognizable classes or motifs. It is possible to model the three-dimensional structure of protein based on homology to a related protein of known structure. Examples are known where two proteins that have relatively low sequence homology, but are found to have almost identical three dimensional structure. Such homologous variants are also included in PLPPs of the present invention.

Once a Picornavirus L proteinase structure or characteristics have been determined using the above analysis, PLPPs can be recombinantly or synthetically produced, or optionally purified, to provide commercially useful amounts of PLPPs for use in diagnostic or research applications, according to known method steps (see, e.g., Ausubel, infra, and Sambrook, infra, which references are herein entirely incorporated by reference).

Recombinant Cloning and/or Production of PLPPs

Known method steps for synthesizing oligonucleotides probes useful for cloning and expressing DNA encoding a PLPP of the present invention, based on the teaching and guidance presented herein, are disclosed by, for example, Ausubel, infra; Sambrook, infra; and Wu et al., *Prog. Nucl. Acid. Res. Molec. Biol.* 21:101–141 (1978), which references are entirely incorporated herein by reference.

A suitable oligonucleotide, or set of oligonucleotides, which is capable of encoding (or which is complementary to a sequence encoding) a PLP fragment of an L proteinase gene is identified as above, synthesized, and hybridized by means well known in the art, against a DNA or, more preferably, a cDNA preparation derived from cells having Picornavirus genes and which are capable of expressing a PLP. Single stranded oligonucleotide probes complementary to an L proteinase activity encoding sequence can be synthesized using method steps (see, e.g., Ausubel, infra; Sambrook, infra).

Such a labeled, detectable probe can be used by known procedures for screening a genomic or cDNA library as described above, or as a basis for synthesizing PCR probes for amplifying a cDNA generated from an isolated RNA encoding a target nucleic acid or amino acid sequence. As a further non-limiting example, transformants can be selected for expression by a host cell of a target protein, by use of selection media appropriate to the vector used, RNA analysis or by the use of antibodies specific for a target protein as a PLPP used in a method according to the present invention.

A target, detectably labeled probe of this sort can be a fragment of an oligonucleotide that is complementary to a polynucleotide encoding a target protein, as a PLPP. Alternatively, a synthetic oligonucleotide can be used as a target probe which is preferably at least about 10 nucleotides in length (such as 10, 15, 16, 17, 18, 19, 20, 21, 22, 23, 24, 25, 26, 27, 28, 29, 30, 35, 40, 45, 50, 60, 70, 80, 90, 100, or more, or any combination or range therein, in increments of 1 nucleotide), in order to be specific for a target a nucleic acid to be detected, amplified or expressed. The probe can correspond to such lengths of a DNA or RNA encoding a PLP, such as a sequence corresponding to a portion of SEQ ID NO:1, wherein the probe sequence is selected according to the host cell containing the DNA, e.g., as presented in Table A1.4 of Ausubel, infra. PLPP encoding nucleic acids of the present invention can include 150–1500, such as 150–1005, 150–1002, 300–600, and 900–1500 nucleotides, or any range or value therein; such as 900–1005, substantially complementary to a portion of nucleotides 3–1007 or 6–1007 of SEQ ID NO:1, wherein the codons can be substituted by codons encoding the same or conservatively substituted amino acids, as well known in the art.

Culturing of the host and induction of protein expression can be induced by methods known per se. A nucleic acid sequence encoding a PLPP, as a Picornavirus L proteinase or variant, of the present invention can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, infra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression of Picornavirus L proteinase or variant in recoverable amounts. The precise nature of the regulatory regions needed for gene expression can vary from organism to organism, as is well known in the analogous art. See, e.g., Sambrook, infra; Ausubel, infra.

The present invention accordingly encompasses the expression of an Picornavirus L proteinase or variant, in prokaryotic cells.

Preferred hosts are bacterial hosts including bacteria, either in vivo, or in situ, such as BL21(DE3)pLysE (pLysE derivative of the *E. coli* strain BL21(DE3)). Other suitable host cells in this context may include bacteria, e.g., of the genera Aeromonas, Aspergillus, Bacillus, Escherichia, Kluyveromyces, Pichia, Rhodococcus, Saccharomyces and Streptomyces. Illustrative of microorganisms used as host cells according to the present invention include, as bacterial cells, *E. coli* and Bacillus (available from the American Type Culture Collection, Rockville, Md.).

Host cells comprising a nucleic acid which encodes a PPLP of the present invention may be grown under conditions that provide expression of a desired polypeptide in recoverable or commercially useful amounts. See, e.g., Ausubel, infra, at §§1 and 13.

For introducing a nucleic acid the present invention into a bacterial cell, known procedures may be used according to the present invention such as by transfection, e.g., using calcium phosphate precipitation, electroporation, DEAE dextran, pelletizing with a DNA gun or using a recombinant phage virus. See, e.g., Ausubel, infra, at §1.8. Other known procedures may also be employed to obtain a recombinant host cell that expresses a heterologous target or folding protein according to the present invention, as will be apparent to those skilled in the art.

In a preferred embodiment, the introduced nucleotide sequence will be incorporated into a plasmid or viral vector capable of autonomous replication in the recipient host. Any of a wide variety of vectors can be employed for this purpose. See, e.g., Ausubel, infra, §§1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Preferred prokaryotic vectors known in the art include plasmids such as those capable of replication in *E. coli* (such as, for example, pET, pBR322, ColE1, pSC101, pACYC 184, πVX), with pET most preferred. Such plasmids are, for example, disclosed by Sambrook, infra; Ausubel, infra). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., *J. Bacteriol.* 169:4177–4183 (1987)), and streptomyces bacteriophages such as ϕC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)); and Ausubel, infra.

As mentioned above, initiation of protein synthesis in FMDV can occur at one of two AUG codons, separated by 84 nucleotides. In one preferred embodiment of the present invention, the initiation of translation at both sites is avoided and only the Lb form is expressed. The T7 RNA polymerase promoter of, e.g., pET11d is followed by the ribosome binding site of the vector, the Lb proteinase itself, VP4 and part of VP2 and two stop codons (FIG. 2). Example 1 describes, in a particularly advantageous embodiment of the present invention, the cloning of nucleotides 892–1896 of the FMDV cDNA (encoding the FMDV leader proteinase Lb form) followed by two stop codons (FIG. 1, 1008–1010 and 1011–1013 of SEQ ID NO:1; derived by amplification by PCR from the plasmid p735; according to known method steps, e.g., Forss et al., *Nucleic. Acids. Res.* 11:7873–7885 (1984)), into the NcoI and BamHI sites of pET11d, as readily available from commercial sources, e.g., (Novagen, Madison, Wis., USA), both restriction sites are reconstituted. The resulting expression plasmid is designated pET11d/FMDV Lb (FIG. 2). Due to constitutive expression of the lac repressor from the vector itself and due to an overlap of the lac operator on the T7 RNA polymerase promotor, efficient repression of the uninduced expression vector can be achieved.

The Lb proteinase containing DNA expression vector can then be transformed into a prokaryotic or eukaryotic host by methods known per se. The present invention further relates to a bacterial host, transformed by the vector containing the DNA sequence capable of expressing an L proteinase.

In a preferred embodiment of the present invention, e.g., as described in Example 1, the expression plasmid is transformed into *E. coli*, preferably BL21(DE3)pLysE (pLysE derivative of the *E. coli* strain BL21(DE3)). Culturing can be performed in standard culturing media, e.g., in LB medium containing ampicillin (100 μg/ml) and chloramphenicol (30 μg/ml) e.g., at 37° C.

In a preferred embodiment of the present invention induction of L proteinase expression in bacterial cells by the pET11d/FMDV Lb vector is performed with IPTG. Preferably the induction is performed between 10° C. and 30° C. with an IPTG concentration between 0.1 mM and 1.0 mM. Most preferred is induction at 15° C. in the presence of 0.4 mM IPTG (see example 1). According to the above described procedure a polyprotein containing the Lb form of the L proteinase can be produced. Most preferably the polyprotein contains the Lb form of the L proteinase, the whole of VP4 and the N-terminal 78 amino acids of VP2. Due to its inherent cis-activity the Lb proteinase cleaves itself off the growing peptide chain, resulting in the accumulation of mature Lb proteinase in the bacteria.

Despite the different catalytic mechanisms of the Lb and 2A proteinases, they have similar molecular masses (20 kDa and 16 kDa, respectively) and similar theoretical isoelectric points (around pI 4.7). This similarity motivated us to employ the purification scheme developed for the 2A proteinases (Liebig et al., *Biochemistry* 32:7581–7588 (1993)) for the Lb proteinase. Surprisingly it was found that this procedure could also be applied for the purification of L proteinases. A preferred embodiment of the present invention is described in Example 2 of the description, which was developed in agreement with the Liebig, infra, protocol.

In one embodiment of the present invention, the cells can be lysed by methods known per se, e.g., sonication and insoluble material can be removed, e.g., by centrifugation preferably at about 40000×g for about 30 min or other methods known by the person skilled in the art. Proteins in solution, can be precipitated, e.g., with about 20% to 50% ammonium sulphate or other methods known per se and the precipitated proteins can be re-dissolved in buffer. Precipitated proteins can be further purified e.g., by column chromatography and other methods known per se to the person skilled in the art. In a preferred embodiment of the present invention, Pharmacia FPLC HR10/10 Mono-Q® column, which can be equilibrated, e.g., with buffer A, can be used. Preferably chromatography steps are performed in a cold room, most preferably at about 4° C.). After washing with a suitable buffer known to the person skilled in the art, elution can be performed with a buffer gradient of increasing ionic strength. Preferably a gradient composed of buffers differing in ionic strength e.g., buffers A and B (buffer B: same as buffer A, except for 1 M NaCl; see Appendix to Examples) can be applied, e.g., 20 ml of 0–20% B, 130 ml of 20–45% B, and 10 ml of 45–100% B. In this preferred embodiment the Lb proteinase elutes at around 250–290 mM NaCl. Fractions containing proteinase can be identified by methods known per se, e.g., SDS-PAGE and/or Western blotting. The Lb proteinase containing fractions can be applied directly to a column. In a preferred embodiment of the present invention a Pharmacia Superdex® 75 Highload 26/60 column can be pre-equilibrated with buffer A. The gel filtration column can also be developed with buffer A. The Lb proteinase elutes with an apparent molecular mass of 20 kDa. Fractions from the $A_{280}$ peak can be examined by methods known per se, e.g., SDS-PAGE. Fractions containing homogenous proteinase can be estimated by methods known per se, e.g., by staining with Coomassie brilliant blue R250. The pooled fractions can then be concentrated by methods known per se, e.g., in an Amicon Centriprep 10 cell concentration in the range of about 30-fold can be achieved. A most preferred embodiment of the present invention is described in example 2 of the description.

The analysis by SDS-PAGE of a typical purification of Lb proteinase according to example 2 is shown in FIG. 3. Yields of recombinant Lb proteinase are about 6.5 mg from 3.5 g of *E. coli* (wet weight). Although the Lb protein elutes as one peak from the gel filtration column, two bands are clearly visible on a Coomassie brilliant blue stained SDS-polyacrylamide gel; both bands are recognized by an antiserum specific for the L proteinase (Strebel, K. et al., *J. Virol.* 59:983–991 (1986)). The two bands can be observed independent of the preparation or temperature at which the protein was expressed (e.g., 15° C. or 30° C.); no change in the ratio of the two bands was detectable during purification (FIG. 3). Furthermore, labelling experiments performed by methods known per se, e.g., in the presence of $^{35}S$ methionine showed that both bands were present 10 min after induction, other labelling methods are known per se.

The protein concentrations of Lb proteinase-containing fractions can be measured by methods known per se, e.g., using the method of Bradford (Bradford, M. *Anal. Biochem.* 72:248–254 (1976)); the concentration of purified Lb proteinase can be determined e.g., using the absorbance at 280 nm. The 6 tryptophan and 7 tyrosine residues e.g., give a molar extinction coefficient at 280 nm of about 41 700 $M^{-1}$ $cm^{-1}$ (Fasman, G. D. (ed). CRC handbook of biochemistry and molecular biology, 3rd. ed., vol 1, pp 187–189. CRC Press, Inc., Boca Raton, Fla. (1977)).

N-terminal amino acid sequencing (determined by automated gas phase Edman degradation) of the purified protein reveals one amino acid sequence; this corresponds exactly to the N-terminal sequence of the Lb proteinase predicted from the nucleotide sequence (FIG. 1 and SEQ ID NO:2). The ability to produce milligram amounts of pure L proteinase is essential to allow an exact characterization of L proteinase substrate specificity and its inhibitor profile.

It is a general aim of the present invention to provide a method for the analysis of the cleavage of eukaryotic elongation factor eIF-4γ or variant thereof by picornavirus L proteinases or variants thereof.

A specific aim of the present invention is to provide a method comprising the analysis of the cleavage of eukaryotic elongation factor eIF-4γ or variant thereof by Lb proteinase or variant thereof. Said method can be used for the identification of inhibitory substances of picornavirus L proteinases.

In a preferred embodiment of the present invention the cleavage of eIF-4γ by Lb proteinase was tested in cytoplasmic cell extracts of IBRS-2 and HeLa cells. In examples 4 and 5 preferred embodiments of the present invention are described. Reactions can be performed in a suitable buffer known to the person skilled in the art, e.g., buffer A. Preferably 1 μg to 50 μg cytoplasmic IBRS-2 or HeLa cell extract (prepared according to Liebig, H.-D. et al., *Biochemistry* 32:7581–7588 (1993)) can be incubated with 0.1 μg to 10 μg purified Lb proteinase at 10° C. to 37° C. most preferably at 30° C. and reactions can be terminated by the addition of e.g., Laemmli sample buffer after e.g., 5, 10, 30 and 60 minutes. The proteins can be separated e.g., by SDS-PAGE preferably on a gel containing 6% acrylamide. The gel can be blotted e.g., onto nitrocellulose and probed with a rabbit anti-eIF-4γ antiserum most preferably e.g., with the peptide 7 antiserum as described in Liebig, H.-D. et al., *Biochemistry* 32:7581–7588 (1993).

According to Example 4, the eIF-4γ protein is found as a series of bands at around 220 kDa (FIG. 4, lane C); upon incubation with Lb proteinase, the material at 220 kDa disappears and three to four bands at a position corresponding to about 130 kDa appear (FIG. 4 lanes 5',10',30', and 60'). These eIF-4γ cleavage products resemble with respect to their electrophoretic mobility and immunologic properties the N-terminal products of cleavage products of eIF-4γbγ proteinase and were designated $cp_a$ accordingly (Lamphear, B. J. et al., *J. Biol. Chem.* 268:19200–19203 (1993)).

According to Example 5, after 10 or 60 min both active viral proteinases produced the characteristic $cp_a$ N-terminal fragments (FIGS. 5A and 5B); $cp_a$ fragments were faintly visible with the C106S HRV2 2A mutant, but only after 16 hours incubation. However, prolonged incubation of the $cp_a$ products with both HRV2 2A or Lb proteinases led to further modifications. 16 hours incubation with HRV2 2A proteinase resulted in the fastest migrating N-terminal product becoming dominant. In the case of 16 hours incubation with the Lb proteinase, primary eIF-4γ cleavage products underwent complete proteolysis (or were too small to be resolved on the gel). In a preferred embodiment of the present invention the Lb proteinase cleavage of eIF-4γ can be analyzed using purified eIF-4 preparations followed by separation of cleavage products.

According to Example 6, purified eIF-4γ, e.g., from rabbit reticulocytes, can be incubated with Lb proteinase and the reaction time course analyzed (FIG. 6A). Reactions for kinetic measurements can contain Lb proteinase preferably at a concentration range of 1 μg/ml to 1 mg/ml (e.g., 11 μg/ml can be particularly preferred) and eIF-4γ (prepared as described; Lamphear, B. J. et al., *J. Biol. Chem.* 268:19200–19203 (1993)) at a concentration range of 1 μg/ml to 1 mg/ml (e.g., 44 μg/ml can be particularly preferred) e.g., in 20 mM MOPS, pH 7.6, 10% glycerol (v/v), 200 mM KCl, 0.25 mM dithiothreitol, 0.1 mM EDTA, and 0.05% Tween® 20. Incubation can be performed at 10° C. to 37° C., most preferably at 30° C. Aliquots can be removed after certain times, e.g., after 0, 1, 3, 5, 10, 20, 30, 40, 50, and 60 min, and analyzed e.g., by SDS-PAGE on 6.5% Gels e.g., by silver staining (FIG. 6A) or immunoblotting, e.g., with the rabbit anti-eIF-4γ peptide 6 antiserum against a synthetic peptide from the C-terminus of eIF-4γ (FIG. 6B; see also FIG. 7; and Liebig, H.-D. et al., *Biochemistry* 32:7581–7588 (1993)).

According to Example 6, after one minute, over 90% of the eIF-4γ is converted to the characteristic cleavage products ranging in size from 100 to 130 kDa (FIG. 6; $cp_a$ and $cp_b$; Lamphear, B. J. et al., *J. Biol. Chem.* 268:19200–19203 (1993)). The primary cleavage products are electrophoretically identical to those obtained with 2A proteinases of HRV2 (Lamphear, B. J. et al., *J. Biol. Chem.* 268:19200–19203 (1993)). Therefore the products can be designated as $cp_a$ and $cP_b$.

Both $cp_a$ and $cp_b$ cleavage products produced by the Lb proteinase can undergo further proteolysis; as with eIF-4γ in HeLa cytoplasmic cell extracts, complete proteolysis of rabbit reticulocyte eIF-4γ can be obtained with this proteinase. However, intermediates in degradation process are observed e.g., as shown in FIG. 6. $cp_a$ cleavage products were subsequently found at 80–110 kDa (FIG. 6A) whereas immunoblotting with rabbit anti-eIF-4γ peptide 6 (C-terminus) antiserum reveals two secondary cleavage products from $cp_b$ of molecular mass 50 and 55 kDa (FIG. 6B).

A specific aim of the present invention is to provide a method comprising the determination of the primary L proteinase cleavage site on eukaryotic elongation factor eIF-4γ or variant thereof. Said method can be used e.g., for the identification of specific inhibitory substances of eIF-4γ site specific cleavage by picornavirus L proteinase.

The primary L proteinase cleavage site of eIF-4γ can be determined by cleavage of purified eIF-4 or purified eIF-4γ, separation of the resulting cleavage products and subsequent sequencing of the cleavage products.

According to Example 7, the cleavage products resulting from incubation of preferably about 100 μg of purified eIF-4 (prepared as described, e.g., in Lamphear, B. J. et al.,*J. Biol. Chem.* 268:19200–19203 (1993)) with preferably about 15 μg of purified Lb proteinase for about 3 min at a temperature of about 30° C. in a buffer e.g., 20 mM MOPS, pH 7.6, 10% glycerol (v/v), 200 mM KCl, 0.25 mM dithiothreitol, 0.1 mM EDTA, and 0.05% Tween® 20 can be used for further sequence analysis (under these conditions, less than 5% of the intact eIF-4γ remained but no appearance of secondary cleavage products could be detected).

Products can be fractionated by methods known to the person skilled in the art e.g., by reverse phase HPLC or by gradient centrifugation. Reactions containing proteinase-treated eIF-4 or eIF-4γ can be applied directly e.g., to an HPLC-column preferably a 0.45×15-cm Vydak C4 column preferably equilibrated in buffer C (preferred volume 2 ml; 0.1% aqueous trifluoroacetic acid). The column can be developed e.g., with buffer C, followed by a linear gradient of buffer C to 80% buffer D (0.1% trifluoroacetic acid in 95% acetonitrile), followed by a gradient to 100% buffer D. The HPLC fractions containing the C-terminal fragment can be identified e.g., by testing with a anti-eIF-4γ antiserum, preferably with the rabbit anti-eIF-4γ peptide 6 (see FIG. 7) antiserum as described in Lamphear, B. J. et al., *J. Biol. Chem.* 268:19200–19203 (1993). Cleavage products derived from the C-terminus ($cp_b$) can be subjected to amino acid sequencing e.g., automated Edman degradation, for determination of N-terminal sequence. The use of an automated sequencer, e.g., an Applied Biosystems model 470A sequenator can be preferred.

According to Example 7, the amino acid sequence RPALSSRGPP which is the exact sequence of rabbit eIF-4γ from amino acid residues 480–489 (SEQ ID NO:8; GenBank accession number L22090) was determined as the N-terminal sequence of the primary eIF-4γ cleavage product of Lb proteinase. This corresponds to the sequence 479-RTTLSTRGPP-488 of the human eIF-4γ sequence (Yan R., W. et al., *J. Biol. Chem.* 267:23226–23231 (1992), GenBank accession number D12686; SEQ ID NO:7). Thus, the primary cleavage of the FMDV Lb proteinase on rabbit eIF-4γ occurs between Gly479 and Arg480, as shown in FIG. 7. As the HRV2 2A proteinase cleaves between Arg486 and Gly487, the cleavage sites are not identical.

Although the primary cleavage products of Lb and HRV2 2A proteinases are electrophoretically identical (e.g., see FIGS. 5A and 5B, under the conditions applied differences in.mobility shifts due to differences of less than 10 amino acids can not be resolved), they can be produced by proteolysis at sites which differ by seven amino acids, as shown in FIG. 7. The use of different sites for the cleavage of eIF-4γ by the L and 2A proteinases implies the presence of a structure which is particularly susceptible to proteolysis. Perhaps this is a region which lies between two hypothetical functional domains of eIF-4γ. Cleavage at such a region between these two functional domains by a viral proteinase would separate them and eliminate eIF-4γ function.

Therefore the present invention also relates to a method of cleavage of eIF-4γ or variant thereof by a picornavirus proteinase or variant thereof comprising the cleavage of eIF-4γ or variant thereof by a picornavirus proteinase or variant thereof between two protein domains linked by an amino acid sequence homologous to the amino acids 472 to 494 of rabbit eIF-4γ or 471 to 493 of human eIF-4γ or linked by an amino acid sequence having the amino acid motifs LGRP (amino acids 7–10 of SEQ ID NO:8), LGRT (amino acids 7–10 of SEQ ID NO:5) or SRGP (amino acids 7–10 of SEQ ID NO:4), wherein cleavage occurs between either G and R or R and G.

A further difference between the eIF-4γ cleavage sites of Lb and HRV2 2A proteinases is the lack of similarity between the cleavage sites of the Lb proteinase on eIF-4γ and on the viral polyprotein where cleavage occurs between the amino acids 206 (K) and 207 (G) of the peptide AKVQRKLKGAGQSSPA (SEQ ID NO:6, and Example 8) spanning the junction between the L and VP4 regions of the FMDV polyprotein (FIG. 7)); the 2A proteinase cleavage site on eIF-4γ is closely related to that on the viral polyprotein (Lamphear, B. J. et al., *J. Biol. Chem.* 268:19200–19203 (1993); Sommergruber, W., et al., *Virology* 198:741–745 (1994)). Furthermore, the Lb proteinase cleavage site on eIF-4γ is unusual in that the P1' residue is arginine and not glycine; the sequence data were unambiguous (see also the cleavage of the synthetic peptide p220-6 (SEQ ID NO:5) in Example 8).

The above described identification of the L proteinase specific cleavage site on eIF-4γ and the disclosed experimental systems provide the person skilled in the art with the necessary information to investigate this cleavage event with respect to e.g., preferred concentrations of L proteinase and eIF-4γ protein, ionic conditions, temperature and so on. Thus the present invention relates in general to any method for analyses of the L proteinase site specific cleavage of eIF-4γ or variant thereof.

It is a further general aim of the present invention to provide a method for the identification of inhibitory substances of picornavirus L proteinases. A more specific aim of the present invention is to provide a method for the identification of inhibitory substances of FMDV L proteinase site specific cleavage of eIF-4γ or variant thereof.

In a preferred embodiment of the present invention the analysis of the cleavage of eIF-4γ or variant thereof by Lb proteinase or variant thereof is performed in the presence of putative inhibitory substances.

The term "putative inhibitory substances" refers to all substances that are able to influence the cleavage of a peptide or protein by Lb proteinase. In particular it refers to any substance that is able to influence the site specific cleavage of eIF-4γ by L proteinase or prevent said site specific cleavage e.g., by preventing the formation of the proteinase substrate interaction, by influencing the kinetic parameters of the cleavage, by binding to the reaction partners, by modifying the reaction partners, etc.

One embodiment of the present invention relates to a method for the identification of inhibitory substances of L proteinase catalyzed cleavage of eIF-4γ, comprising incubation of purified eIF-4γ together with a putative inhibitory substance in the presence of L proteinase, or preferable Lb proteinase, in a suitable buffer. The resulting products can be analyzed by methods known to the person skilled in the art. For a detailed description of preferred reaction conditions, see Examples 6 and 7, as presented below.

In another embodiment of the present invention, instead of purified eIF-4γ, eukaryotic cell extracts containing eIF 4 are incubated in the presence of a putative inhibitory substance together with Lb proteinase. After incubation the products can be analyzed by methods known to the person skilled in the art, for detailed description of preferred reaction conditions see example 4 and 5 of the description.

The present invention further relates to synthetic peptides that contain amino acid motifs susceptible for cleavage by L proteinase.

In a preferred embodiment of the present invention, shown in example 8, incubation of each of the synthetic peptides shown in Table 3, (P89 (SEQ ID NO:3), p220-4 (SEQ ID NO:4), p220-6 (SEQ ID NO:5) or LVP4-1 (SEQ ID NO:6)) together with Lb proteinase results in cleavage of the respective peptide. Incubation is preferred e.g., at a concentration of 100 μM peptide in 50 mM Tris/HCl (pH 8.0), 150 mM NaCl, 1 mM EDTA, and 5 mM DTT in the presence of 10 μg/ml Lb proteinase at 37° C. for 4, 8, 16, 32 or 64 min. The time course of the cleavage of peptides LVP4-1, p220-4, p220-6, and the N-terminally acetylated and C-terminally aminated peptide P89 is shown FIG. 8. Peptide LVP4-1 was most efficiently cleaved by Lb with more than 80% cleavage after 4 min and about 90% cleavage after 8 min. Cleavage sites of each peptide respectively are shown in Table 3.

p220-4 includes the native cleavage region for proteinases 2A of HRV2 and CoxB4; this peptide was cleaved between amino acids Arg and Gly (Table 3) as shown for HRV2 2A proteinase, indicating that depending on the individual synthetic peptide also different sites than the native cleavage site on eIF-4γ can be utilized for cleavage by Lb proteinase. Interestingly the cleavage region for intramolecular processing for 2A proteinase presented by peptide P89 could also be processed by Lb proteinase. For Lb proteinase the cleavage seems not to occur at the Ala-Gly site as it was shown for HRV2 2A, as the migration profile on the HPLC column indicated, only one or two amino acids are cleaved from the N-terminus. Cleavage is expected to be up- or downstream of the Arg in P89 (see also Table 3).

In conclusion preferred amino acid motifs containing L proteinase cleavage sites are peptides homologous to the peptides P89 (SEQ ID NO:3), p220-4 SEQ ID NO:4), p220-6 (SEQ ID NO:5) or LVP4-1 (SEQ ID NO:6). Preferred cleavage sites are for example the sequence motifs LGRP (amino acids 7–10 of SEQ ID NO:8), LGRT (amino acids 7–10 of SEQ ID NO:5), TRGP (amino acids 7–10 of SEQ ID NO:4), TRPI (amino acids 1–4 of SEQ ID NO:3)

and LKGA (amino acids 7–10 of SEQ ID NO:6). Most preferably the peptide bond between amino acids G and R, R and G, R and P or K and G is cleaved by L proteinase.

Figure 3:
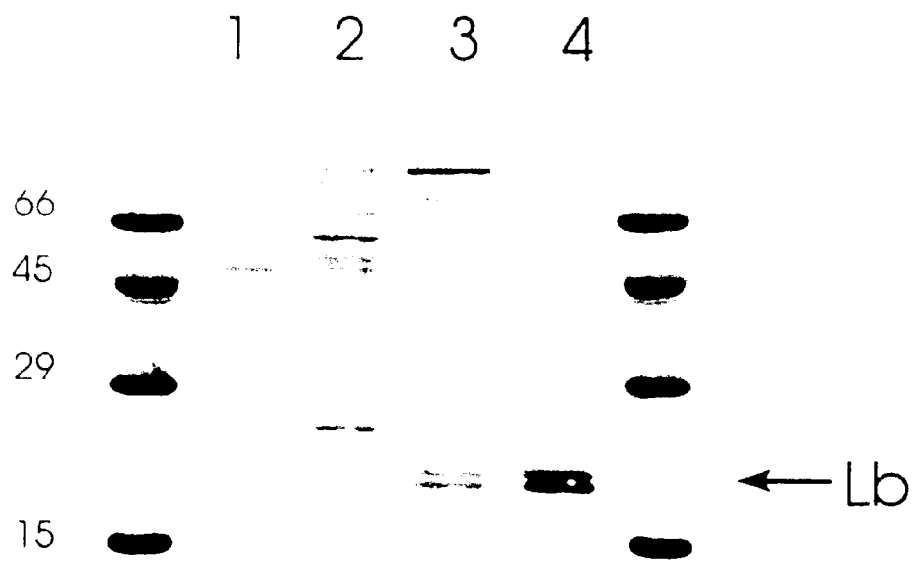
FIG. 3. SDS-PAGE analysis of the purification of recombinant FMDV Lb proteinase. Two micrograms of total protein each from the indicated fractions were applied to gel containing 15% acrylamide; visualization was with Coomassie brilliant blue R250. The numbers on the left indicate apparent molecular sizes (in kDa). The arrow indicates the Lb protein.

The cleavage of synthetic peptide LVP4-1 as described in example 8 is a further confirmation that the recombinant Lb proteinase of the present invention possesses the activity of cleaving itself off the growing polypeptide chain between its own C-terminus and the N-terminus of VP4 as described by Strebel & Beck, *J. Virol.* 58:893–899 (1986). Although this is already apparent in view of the electrophoretic mobility of the purified Lb proteinase, as this protein migrates with a molecular mass of 20 kDa and not of 34 kDa as expected for the non-processed product containing Lb, VP4 and part of VP2 (FIG. 3).

A further aim of the present invention is to provide a method for the identification of inhibitory substances of picornavirus L proteinase, comprising the analysis of the cleavage of synthetic peptides by Lb proteinase or variant thereof in the presence of putative inhibitory substances.

In a preferred embodiment of the present invention a test system for the identification of inhibitors of L proteinase is disclosed in example 9. According to example 9, the synthetic peptide LVP4-1 (SEQ ID NO:6; synthesis of peptide substrates, their purification and the mode of kinetic studies utilizing HPLC were as described in Sommergruber et al., *J. Biol. Chem.* 267:22639–22644 (1992)) is incubated at a concentration of about 100 $\mu$M in 50 mM Tris/HCl (pH 8.0), 150 mM NaCl, 1 mM EDTA, and 5 mM DTT in the presence of 0.5% SDS for 1 min. Then 10, 20, 40 or 80 $\mu$g/ml Lb proteinase is added and incubation is performed at 37° C. for 64 min. Analysis of reaction products can be performed e.g., as described in example 8. No cleavage of peptide LVP4-1 could be detected. Controls performed under identical conditions in the absence of SDS showed complete cleavage of the LVP4-1 peptide after 64 min.

In other preferred embodiments of the present invention e.g., peptides P89 (SEQ ID NO:3), p220-4 (SEQ ID NO:4), and p220-6 (SEQ ID NO:5) are tested exactly as described above. As shown in example 9, in the presence of 0.5% SDS complete inhibition of cleavage of the respective peptide was observed, whereas in the absence of SDS efficient cleavage was detected.

The Lb proteinase site specific cleavage of proteins or peptides and subsequent purification of the resulting cleavage products leads to new proteins or peptides.

Therefore the present invention also relates to the products derived by the Lb proteinase site specific cleavage of a protein or peptide containing an amino acid sequence motif with homology to the L proteinase cleavage site on eIF-4$\gamma$ or with homology to at least one of the synthetic peptides according to SEQ ID NO:4 or 5.

Having now generally described the present invention, the same will be more readily understood through reference to the following example which is provided by way of illustration, and is not intended to be limiting of the present invention.

EXAMPLES

Example 1

Expression of FMDV Leader Proteinase Lb Form

A DNA segment containing nucleotides 892–1896 of the FMDV cDNA followed by two stop codons (FIG. 1, SEQ ID NO:1; derived by amplification by PCR from the plasmid p735; Forss, S. et al., *Nucleic. Acids. Res.* 11:7873–7885 (1984)), was cloned into the NcoI and BamHI sites of pET11d (Studier, F. W. et al., *Methods Enzymol.* 185:60–89 (1990)); as the overlapping ends of the NcoI and BamHI sites were filled in with the Klenow fragment *E. coli* DNA-Polymerase I before ligation, both restriction sites are reconstituted. The resulting expression plasmid is designated pET11d/FMDV Lb (FIG. 2). The Lb proteinase containing DNA expression vector was transformed into *E. coli*, BL21(DE3)pLysE (pLysE derivative of the *E. coli* strain BL21(DE3)). Culturing was performed in LB medium containing ampicillin (100 $\mu$g/ml) and chloramphenicol (30 $\mu$g/ml) at 37° C. Induction was performed with 0.4 mM IPTG at 15° C. A polyprotein containing the Lb form of the L proteinase was produced. The polyprotein contains the L proteinase Lb form, the whole of VP4 and the N-terminal 78 amino acids of VP2 (as indicated in FIG. 1). Self cleavage of the L proteinase off the growing peptide chain, resulted in the accumulation of mature Lb proteinase in the bacteria.

Remarks

As mentioned before, the expression of viral proteinases has generally proved to be difficult for two reasons. Firstly, most (including the HIV proteinase, rhino- and enteroviral 2A proteinases) are toxic for the *E. coli* cell; secondly, these proteins are insoluble at high levels of expression. Both problems were encountered with the Lb proteinase; they were solved using the experience gained in expressing the 2A proteinase of HRV2. However, the Lb proteinase appeared to be more toxic than these 2A proteinases, as even the small amounts of non-repressed expression present using the vector pET8c in the *E. coli* BL21(DE3)LysE strain led to rapid loss of expression.

Example 2

Purification of FMDV Leader Proteinase Lb Form

The purification procedure was performed in agreement to the purification procedure of Liebig et al. (Liebig, H.-D. et al., *Biochemistry* 32:7581–7588 (1993)) which had been proven useful for the purification of 2A proteinases.

The cells were lysed by sonication and insoluble material was removed by centrifugation (40000×g, 30 min) to give fraction 1. Proteins of fraction 1 precipitating between 20% and 50% ammonium sulphate were re-dissolved in buffer A (50 mM NaCl, 50 mM Tris-HCl (pH 8.0 at 20° C.), 1 mM EDTA, 5 mM DTT , and 5% glycerol) to give fraction 2. This fraction was then loaded onto a Pharmacia FPLC HR10/10 Mono-Q® column which had been pre-equilibrated with buffer A, (all chromatography steps were performed at 4° C.). After the column had been washed with 4 bed volumes of buffer A, the following gradient composed of buffer A and buffer B (same as buffer A, except for 1 M NaCl) was applied: 20 ml of 0–20% B, 130 ml of 20–45% B, and 10 ml of 45–100% B. The Lb proteinase eluted at around 250–290 mM NaCl. Fractions containing proteinase were identified by SDS-PAGE and Western blotting with an antiserum specific for the L proteinase (Strebel, K. et al., *J. Virol.* 59:983–991 (1986)), pooled (fraction 3), and applied directly to a Pharmacia Superdex® 75 Highload 26/60 column pre-equilibrated with buffer A. The gel filtration column was developed with buffer A. The Lb proteinase eluted with an apparent molecular mass of 20 kDa. Fractions from the $A_{280}$ peak were examined by SDS-PAGE, and those containing proteinase at a purity of more than 98% (estimated after staining with Coomassie brilliant blue R250) were pooled and concentrated about 30-fold in an Amicon Centriprep 10 cell. The protein concentrations of Lb-containing fractions were measured using the method of Bradford (Bradford, M., *Anal. Biochem.* 72:248–254 (1976)); the concentration of purified Lb proteinase was determined using the absorbance at 280 nm. The 6 tryptophan and 7 tyrosine residues give a molar extinction coefficient at 280 nm of about 41 700 $M^{-1}$ $cm^{-1}$ (Fasman, G. D. (ed). CRC handbook of biochemistry and molecular biology, 3rd. ed., vol 1, pp 187–189. CRC Press, Inc., Boca Raton, Fla. (1977)). The analysis by SDS-PAGE of a typical purification of Lb proteinase is shown in FIG. 3. Yields of recombinant Lb proteinase were about 6.5 mg from 3.5 g of *E. coli* (wet weight). Although the Lb protein elutes as one peak from the gel filtration column, two bands are clearly visible on a Coomassie brilliant blue stained SDS-polyacrylamide gel; both bands were recognized by an antiserum specific for the L proteinase (see above). The two bands were always observed independent of the preparation or temperature at which the protein was expressed e.g. 15° C. or 30° C.; no change in the ratio of the two bands was detectable during purification (FIG. 3). Furthermore, labelling experiments (Studier, F. W. et al., *Methods Enzymol.* 85:60–89 (1990)) in the presence of $^{35}S$ methionine showed that both bands were present 10 min after induction. N-terminal amino acid sequencing (determined by automated gas phase Edman degradation; Hunkapillar & Hood, *Science* 219:650–959 (1983)) of the purified protein revealed one amino acid sequence; this corresponded exactly to the N-terminal sequence of the Lb proteinase (SEQ ID NO:2 and FIG. 1) predicted from the nucleotide sequence beginning at nucleotide 3 of SEQ ID NO:1 and FIG. 1. The Lb preparations always contained two bands, both of which were recognized by an antiserum against the L proteinase. Therefore, we are confident that these bands represent two forms of the Lb proteinase. N- and C-terminal amino acid sequence analyses indicated that the forms can differ at the C-terminus; at least three events might give rise to this. Firstly, the Lb proteinase can have two cleavage sites at the L/VP4 junction. Secondly, the Lb proteinase can be digesting itself during accumulation in the cell; thirdly, the molecule can be processed by *E. coli* proteinases.

Example 3

Intramolecular Cleavage Activity of Lb Proteinase

The intramolecular cleavage activity, in which the recombinant Lb proteinase cleaves itself off the growing polypeptide chain between its own C-terminus and the N-terminus of VP4 (Strebel, K, and E. Beck, *J. Virol.* 58:893–899 (1986)) is apparent, because the recombinant Lb proteinase, expressed as described in example 1, migrates with a molecular mass of 20 kDa and not of 34 kDa as expected for the non-processed product containing Lb, VP4 and part of VP2 (FIG. 3). Further proof, that this intramolecular cleavage is performed by the Lb proteinase, is provided by the cleavage of the synthetic peptide LVP4-1 (SEQ ID NO:6) containing the internal cleavage site of the FMDV polyprotein. In the native polyprotein the peptide bond between the amino acids Lys206 and Gly207 is cleaved by L proteinase. As shown in example 8 the synthetic peptide LVP4-1 is cleaved exactly at this position providing also further proof that the recombinant Lb proteinase according of example 8 has the cleavage specificity of the native enzyme.

Example 4

Lb Proteinase Cleavage of eIF-4γ in Cytoplasmic IBRS-2 Cell Extracts

Reactions (final volume 10 μl) were performed in buffer A: 7.5 μg cytoplasmic IBRS-2 cell extract (prepared as described in Liebig, H.-D. et al., *Biochemistry* 32:7581–7588 (1993)) was incubated with 0.3 μg purified Lb proteinase at 30° C. Reactions were terminated by the addition of Laemmli sample buffer after 5, 10, 30 and 60 minutes. The proteins were separated by SDS-PAGE on a gel containing 6% acrylamide. The gel was blotted onto nitro-cellulose and probed with the rabbit anti-eIF-4γ peptide 7 antiserum as described (Liebig, H.-D. et al. *Biochemistry* 32:7581–7588 (1993)). The eIF-4γ protein was found as a series of bands at around 220 kDa (FIG. 4, lane C); upon incubation with Lb proteinase, the material at 220 kDa disappears and three to four bands at a position corresponding to about 130 kDa appear (FIG. 4 lanes 5',10',30',60'). These eIF-4γ cleavage products resembled with respect to their electrophoretic mobility and immunologic properties the N-terminal products of HRV2 proteinase and were designated $cp_a$ accordingly (Lamphear, B. J. et al., *J. Biol. Chem.* 268:19200–19203 (1993)).

Example 5

Lb Proteinase Cleavage of eIF-4γ in Cytoplasmic HeLa Cell Extracts

Reactions (final volume 10 μl) were performed in buffer A: 7.5 μg cytoplasmic HeLa cell extract (prepared as described in Liebig, H.-D. et al., *Biochemistry* 32:7581–7588 (1993)) was incubated with 1 μg purified Lb proteinase, HRV2 proteinase 2A or active site mutant C106S of HRV2 2A (the HRV2 proteinase 2A and the C106S mutant were prepared as described in Liebig, H.-D. et al., *Biochemistry* 32:7581–7588 (1993) at 30° C. Reactions were terminated by the addition of Laemmli sample buffer after 10 or 60 minutes or 16 hours. The proteins were separated by SDS-PAGE on a gel containing 6% acrylamide. The gel was blotted onto nitro-cellulose and probed with the rabbit anti-eIF-4γ peptide 7 (see also FIG. 7) antiserum as described (Liebig, H.-D. et al., *Biochemistry* 32:7581–7588 (1993)). After 10 or 60 min both active viral proteinases produced the characteristic $cp_a$ N-terminal fragments (FIGS. 5A and 5B); $cp_a$ fragments were faintly visible with the C106S HRV2 2A mutant, but only after 16 hours incubation. However, prolonged incubation of the $cp_a$ products with both HRV2 2A or Lb proteinases led to further modifications. 16 hours incubation with HRV2 2A proteinase resulted in the fastest migrating N-terminal product becoming dominant. In the case of 16 hours incubation with the Lb proteinase, primary eIF-4γ cleavage products underwent complete proteolysis (or were too small to be resolved on the gel).

Example 6

Lb Proteinase Cleavage of eIF-4γ in Purified eIF-4γ Preparations and Separation of Cleavage Products Purified eIF-4γ from rabbit reticulocytes was incubated with Lb proteinase and the reaction time course analyzed (FIG. 6A). Reactions for kinetic measurements contained Lb proteinase (at 11 μg/ml) and eIF-4γ (at 44 μg/ml; prepared as described (Lamphear, B. J. et al., *J. Biol. Chem.* 268:19200–19203 (1993)) in 20 mM MOPS, pH 7.6, 10% glycerol (v/v), 200 mM KCl, 0.25 mM dithiothreitol, 0.1 mM EDTA, and 0.05% Tween 20. Incubation was at 30° C.; aliquots (16 μl) were removed after 0, 1, 3, 5, 10, 20, 30, 40, 50, and 60 min, and analyzed by SDS-PAGE on 6.5% Gels by silver staining (FIG. 6A) or immunoblotting (FIG. 6B; with the rabbit anti-eIF-4γ peptide 6 antiserum against a synthetic peptide from the C-terminus of eIF-4γ (see also FIG. 7) as described in Liebig, H.-D. et al. *Biochemistry* 32:7581–7588 (1993)). After one minute, over 90% of the eIF-4γ was converted to the characteristic cleavage products ranging in size from 100 to 130 kDa (FIG. 6; cp$_a$ and Cp$_b$; Lamphear, B. J. et al., *J. Biol. Chem.* 268:19200–19203 (1993)). The primary cleavage products were electrophoretically identical to those obtained with 2A proteinases of HRV2 (Lamphear, B. J. et al., *J. Biol. Chem.* 268:19200–19203 (1993)). This allowed us to designate the products as cp$_a$ and cp$_b$. Both cp$_a$ and cp$_b$ cleavage products produced by the Lb proteinase underwent further proteolysis; as with eIF-4γ in HeLa cytoplasmic cell extracts, complete proteolysis of rabbit reticulocyte eIF-4γ could be obtained with this proteinase. However, intermediates in degradation process could be observed as shown in FIG. 6. cp$_a$ cleavage products were subsequently found at 80–110 kDa (FIG. 6A) whereas immunoblotting with rabbit anti-eIF-4γ peptide 6 (C-terminus) antiserum revealed 2 secondary cleavage products from cp$_b$ of molecular mass 50 and 55 kDa (FIG. 6B).

Example 7

Determination of the Primary Lb Proteinase Cleavage Site of eIF-4γ

To determine the primary cleavage site cleavage products resulting from incubation of 90 μg of purified eIF-4γ from rabbit reticulocytes (prepared as described in Lamphear, B. J. et al., *J. Biol. Chem.* 268:19200–19203 (1993)) was incubated with 12 μg of purified Lb proteinase for 3 min at 30° C. in 20 mM MOPS, pH 7.6, 10% glycerol (v/v), 200 mM KCl, 0.25 mM dithiothreitol, 0.1 mM EDTA, and 0.05% Tween® 20 (under these conditions, less than 5% of the intact eIF-4γ remained but no appearance of secondary cleavage products could be detected). Samples were fractionated by reverse phase HPLC on a Waters model 625 LC system. Reactions containing proteinase-treated eIF-4 (2 ml) were applied directly to a 0.45×15-cm Vydak C4 column equilibrated in buffer C (0.1% aqueous trifluoroacetic acid). The column was developed with 5 ml of buffer C, a 40-ml linear gradient of buffer C to 80% buffer D (0.1% trifluoroacetic acid in 95% acetonitrile), followed by a 2-ml gradient to 100% buffer D. The HPLC fractions containing the C-terminal fragment were identified by testing with the rabbit anti-eIF-4γ peptide 6 (see FIG. 7) antiserum as described (Lamphear, B. J. et al., *J. Biol. Chem.* 268:19200–19203 (1993)). Cleavage products derived from the C-terminus (cp$_b$) were subjected to automated Edman degradation, for determination of N-terminal sequence, using an Applied Biosystems model 470A sequenator.

The amino acid sequence RPALSSRGPP (see Table 3 and SEQ ID NO:8) which is the exact sequence of rabbit eIF-4γ from amino acid residues 480–489 was determined; (GenBank accession number L22090). This corresponds to the sequence 479-RTTLSTRGPP-488 (SEQ ID NO:7) of the human eIF-4γ sequence (Yan R., W. et al., *J. Biol. Chem.* 267:23226–23231 (1992), GenBank accession number D12686). Thus, the primary cleavage of the FMDV Lb proteinase on rabbit eIF-4γ occurs between Gly 479 and Arg 480, as shown in FIG. 7. As the HRV2 2A proteinase cleaves between Arg 486 and Gly 487, the cleavage sites are not identical. Although the primary cleavage products of Lb and HRV2 2A proteinases are electrophoretically identical (FIGS. 5A and 5B, under the conditions applied, differences in mobility shifts due to differences of less than 10 amino acids cannot be resolved), they are produced by proteolysis at sites which differ by seven amino acids, as shown in FIG. 7. The use of different sites for the cleavage of eIF-4γ by the L and 2A proteinases implies the presence of a structure which is particularly susceptible to proteolysis. Perhaps this is a region which lies between two hypothetical functional domains of eIF-4γ. Cleavage at such a region between these two functional domains by a viral proteinase would separate them and eliminate eIF-4γ function.

A further difference between the eIF-4γ cleavage sites of Lb and HRV2 2A proteinases is the lack of similarity between the cleavage sites of the Lb proteinase on eIF-4γ and on the viral polyprotein where cleavage occurs between the amino acids 206 (K) and 207 (G) of the peptide AKVQRKLKGAGQSSPA (SEQ ID NO:6, see also example 8) spanning the junction between the L and VP4 regions of the FMDV polyprotein (FIG. 7 and Table 3)); the 2A proteinase cleavage site on eIF-4γ is closely related to that on the viral polyprotein (Lamphear, B. J. et al., *J. Biol. Chem.* 268:19200–19203 (1993); Sommergruber, W., et al., *Virology* 198:741–745 (1994)). Furthermore, the Lb proteinase cleavage site on eIF-4γ is unusual in that the P1' residue is arginine and not glycine; the sequence data were unambiguous (see also the cleavage of the synthetic peptide p220-6 (SEQ ID NO:5) in example 8).

Example 8

Lb Proteinase Cleavage of Synthetic Peptides

Each of the synthetic peptides shown in Table 3, P89 (SEQ ID NO:3), p220-4 (SEQ ID NO:4), p220-6 (SEQ ID NO:5) or LVP4-1 (SEQ ID NO:6) (synthesis of peptide substrates, their purification and the mode of kinetic studies utilizing HPLC were as described in Sommergruber et al.,*J. Biol. Chem.* 267:22639–22644 (1992)) was incubated at a concentration of 100 μM in 50 mM Tris/HCl (pH 8.0), 150 mM NaCl, 1 mM EDTA, and 5 mM DTT in the presence of 10 μg/ml Lb proteinase at 37° C. for 4, 8, 16, 32 or 64 min and the reaction products analyzed exactly as described in the published EP 0541 058A1.

TABLE 3

| FMDV LB CLEAVAGE SITES ON INDIVIDUAL PEPTIDES | |
|---|---|
| 1. T P S F A N L G*R P A L S S R G P P R G G P G | amino acids 472 to 494 of rabbit eIF-4γ are shown (SEQ ID NO:7) |
| 2. T P S F A N L G*R T T L S T R G P P R G G P G | amino acids 471 to 493 of human eIF-4γ are shown (SEQ ID NO:8) |
| 3. T P S F A N L G*R T T L S T R G | p220-6 (synthetic peptide from human eIF-4γ) (SEQ ID NO:5) |

TABLE 3-continued

FMDV LB CLEAVAGE SITES ON INDIVIDUAL PEPTIDES

| | |
|---|---|
| 4. G R T T L S T R*G P P R G G P G | p220-4(synthetic peptide from human eIF-4γ) (SEQ ID NO:4) |
| 5. A K V Q R K L K*G A G Q S S P A | LVP4-1(synthetic peptide from FMDV polyprotein) (SEQ ID NO:6) |
|           ? ? | |
| 6. Ac-T*R*P I I T T A G P S D M Y V H-NH$_2$ | P89 (synthetic peptide from HRV2 polyprotein) (SEQ ID NO:3) |

\* indicates cleavage site;
? indicates cleavage position not yet confirmed
Ac indicates acetylated N-terminus;
NH$_2$ indicates aminated C-terminus Peptides LVP4-1, p220-4, p220-6, and the N-terminally acetylated and C-terminally aminated peptide P89 were all cleaved by Lb (Table 3 and FIG. 8). Peptide LVP4-1 was most efficiently cleaved by Lb with more than 80% cleavage after 4 min and about 90% cleavage after 8 min. p220-4 includes the native cleavage region for proteinases 2A of HRV2 and CoxB4 (Lamphear, B. J. et al., *J. Biol. Chem.* 268:19200–19203 (1993); Sommergruber, W., et al., *Virology* 198:741–745 (1994)), this peptide was cleaved between amino acids Arg and Gly (Table 3) as shown for HRV2 2A proteinase, indicating that depending on the individual synthetic peptide also different sites than the native cleavage site on eIF-4γ can be utilized for cleavage by Lb. Interestingly the cleavage region for intramolecular processing for 2A proteinase presented by peptide P89 could also be processed by Lb. For Lb the cleavage seems not to occur at the Ala-Gly site as it was shown for HRV2 2A, as the migration profile on the HPLC column indicated, only one or two amino acids get cleaved of the N-terminus. Cleavage is supposed to be up- or downstream of the Arg in P89 (see also Table 3).

Example 9

Test System for the Identification of Inhibitors of L Proteinases

The synthetic peptide LVP4-1 (SEQ ID NO:6; synthesis of peptide substrates, their purification and the mode of kinetic studies utilizing HPLC were as described in Sommergruber et al., *J. Biol. Chem.* 267:22639–22644 (1992)) was incubated at a concentration of 100 μM in 50 mM Tris/HCl (pH 8.0), 150 mM NaCl, 1 mM EDTA, and 5 mM DTT in the presence of 0.5% SDS for 1 min. Then 10, 20, 40 or 80 μg/ml Lb proteinase was added and incubation was performed at 37° C. for 64 min. Analysis of reaction products was performed exactly as described in example 8. No cleavage of peptide LVP4-1 could be detected. Controls performed under identical conditions in the absence of SDS showed complete cleavage of the LVP4-1 peptide after 64 min. Synthetic peptides P89 (SEQ ID NO:3), p220-4 (SEQ ID NO:4), and p220-6 (SEQ ID NO:5) were tested exactly as described above. In the presence of 0.5% SDS complete inhibition of cleavage of the respective peptide was observed, whereas in the absence of SDS efficient cleavage was detected.

Appendix to Examples

| Reagents | |
|---|---|
| buffer A: | 50 mM NaCl, 50 mM Tris-HCl (pH 8.0 at 20° C.), 1 mM EDTA, 5 mM DTT, and 5% glycerol. |
| buffer B: | 1M NaCl, 50 mM Tris-HCl (pH 8.0 at 20° C.), 1 mM EDTA, 5 mM DTT, 5% glycerol. |
| buffer C: | 0.1% aqueous trifluoroacetic acid. |
| buffer D: | 0.1% trifluoroacetic acid in 95% acetonitrile. |

Restriction endonucleases and DNA modifying enzymes were from New England Biolabs (Beverly, Mass.); reactions were performed as described by the supplier. Oligonucleotide and oligopeptide synthesis was as described (Sommergruber, W., M. et al., *Virology* 169:68–77 (1989), Sommergruber, W., H. et al., *J. Biol. Chem.* 267:22639–22644 (1992)). Rabbit reticulocyte lysate was prepared as described (Adamson, J. D. et al., *J. Mol. Biol.* 42:247–251 (1969)); $m^7$GTP was purchased from Sigma. The C4 column for reverse phase separation of eIF-4γ cleavage products was obtained from Pharmacia LKB Biotechnology. Ammonium sulphate ("suprapure grade") was from Merck, Darmstadt, FRG; all other chemicals were of reagent grade.

pET expression plasmids (Studier, F. W. et al., *Methods Enzymol.* 185:60–89 (1990)) were maintained in the *E. coli* K strain HMS174 ($F^-$ recA $r^-_{K12}m^+_{K12}Rif^R$) and expressed in the pLysE derivative of *E. coli* B strain BL21(DE3) ($F^-$ ompT $r^-_Bm^-_B$) (Studier, F. W. et al., *Methods Enzymol.* 185:60–89 (1990)). Integrated into the chromosome of this strain is one copy of the T7 RNA polymerase gene under the control of the lac operon. In addition, the T7 lysozyme protein, the gene of which is carried episomally, is expressed constitutively. Relatively high levels of T7 lysozyme can be tolerated by *E. coli*; this resistance appears to be due to the inability of the protein to pass through the inner membrane to reach the peptidoglycan layer (Studier, F. W. et al., *Methods Enzymol.* 185:60–89 (1990)).

HRV2 2A Proteinase Expression

The expression vector pET8c/HRV2 2A has been described (Liebig, H.-D. et al., *Biochemistry* 32:7581–7588 (1993)). The expression plasmid pET8c/HRV2 2A(C106S) contains the HRV2 nucleotides 3161–3586 coding for the HRV2 2A proteinase only (Skern, T. et al., *Nucleic Acids Res.* 13:2111–2126 (1985)) cloned into the NcoI and BamHI sites of pET8c. Nucleotides 3477 and 3488 carry G to C and T to A mutations, respectively, resulting in the amino acid change Cys to Ser at the active site. Two stop codons are present after nucleotide 3586. On induction with IPTG, HRV2 2A(C106S) proteinase containing an extra methionine residue at the N-terminus is produced. The purification of HRV2 2A proteinase was as described (Liebig, H.-D. et al., *Biochemistry* 32:7581–7588 (1993)).

Anti-eIF-4γ Peptide Antiserum

Rabbit anti-eIF-4γ peptide 7 antiserum (raised against amino acids 327–342) and rabbit anti-eIF-4γ peptide 6 antiserum (raised against amino acids 1230–1249) were as described (Yan R., W. et al. *J. Biol. Chem.* 267:23226–23231 (1992)). Alkaline phosphatase-conjugated anti-rabbit IgG was purchased from Promega, Madison, Wis. Horseradish peroxidase-conjugated goat anti-rabbit IgG was obtained from Vector Laboratories (Burlingame, Calif.).

General Remarks

Techniques known per se to the artisan skilled in the art are, e.g., described in detail in (Sambrook, J. et al., *Molecular Cloning*, 2nd edition, Cold Spring Harbour Laboratory Press (1989); Ausubel, supra).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the present invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A DNA molecule comprising a DNA vector and a DNA segment encoding at least one Picornavirus L proteinase peptide (PLPP), said DNA segment being operably linked to a T7 promoter, wherein said molecule expresses said PLPP when present in a bacterial host cell to yield soluble PLPP having L proteinase enzymatic activity, and wherein said DNA segment consists of nuclcotides 6–1007 of SEQ ID NO: 1 or a nucleotide sequence complementary thereto.

2. A DNA molecule comprising a DNA vector and a DNA segment encoding at least one Picornavirus L proteinase peptide (PLPP), said DNA segment being operably linked to a T7 promoter, wherein said molecule expresses said PLPP when present in a bacterial host cell to yield soluble PLPP having L proteinase enzymatic activity, and wherein said DNA segment consists of nucleotides 6–1013 of SEQ ID NO: 1 or a nucleotide sequence complementary thereto.

3. A DNA molecule comprising a DNA vector and a DNA segment encoding at least one Picornavirus L Droteinasc peptide (PLPP), said DNA segment being operably linked to a T7 promoter, wherein said molecule expresses said PLPP when present in a bacterial host cell to yield soluble PLPP leaving L proteinase enzymatic activity, and wherein said DNA segment consists of nuclcotides 3–1007 of SEQ ID NO: 1 or a nucleotide sequence complementary thereto.

4. A DNA molecule comprising a DNA vector and a DNA segment encoding at least one Picornavirus L proteinase peptide (PLPP), said DNA segment being operably linked to a T7 promoter, wherein said molecule expresses said PLPP when present in a bacterial host cell to yield soluble PLPP having L proteinase enzymatic activity, and wherein said DNA segment consists of nuclcotides 6–1010 of SEQ ID NO: 1 or a nucleotide sequence complementary thereto.

5. A DNA molecule according to claims 1, 2, 3 or 4, wherein said vector is pET11d.

6. A cell line, comprising a DNA molecule according to claims 1, 2, 3 or 4.

7. A cell line according to claim 6, wherein said host bacterial cell is *E. coli*.

8. A method for the high level expression of the Picornavirus L proteinase polypeptide, comprising:
   (a) transforming a bacterial host cell with the DNA molecule of claims 1, 2, 3 or 4;
   (b) growing the transformed host cell in a culture medium; and
   (c) inducing the expression of said polypeptide.

9. The method according to claim 8, wherein said bacterial host cell is *E. coli*.

10. The method according to claim 9, wherein the *E. coli* host cell strain is BL21(DE3)pLysE.

11. The method according to claim 8, wherein said DNA vector is a pET expression vector.

12. The method according to claim 11, wherein said pET vector is pET11d.

13. The method according to claim 8, wherein said expression of said polypeptide is induced by the addition of IPTG to a final concentration of from 0.1 mM to 1.0 mM.

14. The method according to claim 13, wherein IPTG is added to a final concentration of 0.4 mM.

15. The method according to claim 8, wherein induction is carried out at a temperature of from 10° C. to 30° C.

16. The method according to claim 15, wherein induction is carried out at 15° C.

* * * * *

UNITED STATES PATENT AND TRADEMARK OFFICE
CERTIFICATE OF CORRECTION

PATENT NO. : 6,180,385 B1
DATED : January 30, 2001
INVENTOR(S) : Skern et al.

Page 1 of 1

It is certified that error appears in the above-identified patent and that said Letters Patent is hereby corrected as shown below:

Title page,
Item [54] ("Title"), please delete "I" and insert -- L --.

Column 33,
Line 51, please delete "nuclcotides" and insert -- nucleotides --.
Line 61, please delete "Droteinasc" and insert -- proteinase --.
Line 65, please delete "leaving" and insert -- having --.
Line 66, please delete "nuclotides" and insert -- nucleotides --.

Column 34,
Line 51, please delete "nuclotides" and insert -- nucleotides --.

Column 36,
Line 4, please delete "." after "C" (first occurrence).

Signed and Sealed this

Seventh Day of August, 2001

*Attest:*

NICHOLAS P. GODICI
*Attesting Officer*   Acting Director of the United States Patent and Trademark Office

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 1019 base pairs
        (B) TYPE: nucleic acid
        (C) STRANDEDNESS: double
        (D) TOPOLOGY: linear (ii) MOLECULE TYPE: cDNA (iv) ANTI-SENSE: NO (vii) IMMEDIATE SOURCE: Fig. 1

(xi) SEQUENCE DESCRIPTION: SEQ ID NO:1:

```
CCATGGAGTT AACACTGTAC AACGGTGAGA AGAAGACCTT TTACTCCAGG CCCAACAACC      60

ACGACAACTG CTGGTTGAAC GCCATCCTCC AGTTGTTCAG GTACGTTGAA GAACCATTCT     120

TCGACTGGGT CTACAGTTCG CCTGAGAACC TCACGCTTGA AGCCATCAAG CAGTTGGAGG     180

ATCTCACAGG ACTTGAACTG CATGAGGGTG GACCACCTGC TCTCGTGATC TGGAACATCA     240

AGCACTTGCT CCACACCGGC ATCGGCACCG CCTCGCGACC CAGCGAGGTG TGCATGGTGG     300

ATGGTACGGA CATGTGCTTG GCTGATTTCC ATGCTGGCAT TTTCCTTAAG GGGCAAGAAC     360

ACGCTGTGTT TGCGTGTGTC ACCTCCAACG GGTGGTACGC GATTGACGAT GAGGACTTCT     420

ACCCCTGGAC GCCGGACCCG TCCGACGTTC TGGTGTTTGT CCCGTACGAT CAAGAACCAC     480

TCAACGGGGA ATGGAAAGCC AAGGTTCAAC GCAAGCTCAA AGGGGCTGGA CAATCCAGTC     540

CAGCGACCGG CTCGCAGAAC CAATCTGGCA ATACTGGCAG CATAATAAAC AACTACTACA     600

TGCAGCAGTA TCAAAACTCC ATGGACACAC AGCTTGGTGA CAACGCAATC AGTGGAGGCT     660

CTAACGAGGG CTCCACCGAC ACAACCTCCA CCCACACAAC CAACACCCAG AACAATGACT     720
```

```
GGTTCTCCAA ACTTGCCAGC TCTGCTTTCA GCGGTCTTTT CGGCGCTCTT CTCGCCGACA      780

AGAAGACAGA GGAGACCACT CTCCTCGAAG ACCGCATCCT CACCACCCGT AACGGCCACA      840

CCACGTCGAC AACCCAGTCA AGCGTTGGAG TCACATACGG GTACGCAACA GCTGAAGATT      900

TTGTGAGCGG ACCGAACACT TCCGGTCTCG AAACCAGAGT TGTGCAGGCA GAACGGTTTT      960

TCAAAACCCA CCTCTTCGAC TGGGTCACCA GTGACTCATT CGGACGTTGA TAAGGATCC     1019
```

(2) INFORMATION FOR SEQ ID NO:2:

(i) SEQUENCE CHARACTERISTICS:
        (A) LENGTH: 335 amino acids
        (B) TYPE: amino acid
        (C) STRANDEDNESS: single
        (D) TOPOLOGY: linear (ii) MOLECULE TYPE: peptide (vii) IMMEDIATE SOURCE: Fig. 1

(xi) SEQUENCE DESCRIPTION: SEQ ID NO:2:

```
Met Glu Leu Thr Leu Tyr Asn Gly Glu Lys Lys Thr Phe Tyr Ser Arg
 1               5                  10                  15

Pro Asn Asn His Asp Asn Cys Trp Leu Asn Ala Ile Leu Gln Leu Phe
                20                  25                  30

Arg Tyr Val Glu Glu Pro Phe Asp Trp Val Tyr Ser Ser Pro Glu
        35                  40                  45

Asn Leu Thr Leu Glu Ala Ile Lys Gln Leu Glu Asp Leu Thr Gly Leu
     50                  55                  60

Glu Leu His Glu Gly Gly Pro Pro Ala Leu Val Ile Trp Asn Ile Lys
65                  70                  75                  80

His Leu Leu His Thr Gly Ile Gly Thr Ala Ser Arg Pro Ser Glu Val
                85                  90                  95

Cys Met Val Asp Gly Thr Asp Met Cys Leu Ala Asp Phe His Ala Gly
                100                 105                 110

Ile Phe Leu Lys Gly Gln Glu His Ala Val Phe Ala Cys Val Thr Ser
            115                 120                 125

Asn Gly Trp Tyr Ala Ile Asp Asp Glu Asp Phe Tyr Pro Trp Thr Pro
        130                 135                 140

Asp Pro Ser Asp Val Leu Val Phe Val Pro Tyr Asp Gln Glu Pro Leu
145                 150                 155                 160

Asn Gly Glu Trp Lys Ala Lys Val Gln Arg Lys Leu Lys Gly Ala Gly
                165                 170                 175

Gln Ser Ser Pro Ala Thr Gly Ser Gln Asn Gln Ser Gly Asn Thr Gly
            180                 185                 190

Ser Ile Ile Asn Asn Tyr Tyr Met Gln Gln Tyr Gln Asn Ser Met Asp
        195                 200                 205

Thr Gln Leu Gly Asp Asn Ala Ile Ser Gly Gly Ser Asn Glu Gly Ser
    210                 215                 220

Thr Asp Thr Thr Ser Thr His Thr Thr Asn Thr Gln Asn Asn Asp Trp
225                 230                 235                 240

Phe Ser Lys Leu Ala Ser Ser Ala Phe Ser Gly Leu Phe Gly Ala Leu
                245                 250                 255

Leu Ala Asp Lys Lys Thr Glu Glu Thr Thr Leu Leu Glu Asp Arg Ile
            260                 265                 270

Leu Thr Thr Arg Asn Gly His Thr Thr Ser Thr Thr Gln Ser Ser Val
        275                 280                 285
```

```
Gly Val Thr Tyr Gly Tyr Ala Thr Ala Glu Asp Phe Val Ser Gly Pro
    290             295                 300
Asn Thr Ser Gly Leu Glu Thr Arg Val Val Gln Ala Glu Arg Phe Phe
305                 310                 315                 320
Lys Thr His Leu Phe Asp Trp Val Thr Asp Ser Phe Gly Arg
                325                 330             335
```

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (P89)

(xi) SEQUENCE DESCRIPTION: SEQ ID NO:3:

```
Thr Arg Pro Ile Ile Thr Thr Ala Gly Pro Ser Asp Met Tyr Val His
1               5                   10                  15
```

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (p220-4)

(xi) SEQUENCE DESCRIPTION: SEQ ID NO:4:

```
Gly Arg Thr Thr Leu Ser Thr Arg Gly Pro Pro Arg Gly Gly Pro Gly
1               5                   10                  15
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (p220-6)

(xi) SEQUENCE DESCRIPTION: SEQ ID NO:5:

```
Thr Pro Ser Phe Ala Asn Leu Gly Arg Thr Thr Leu Ser Thr Arg Gly
1               5                   10                  15
```

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (LVP4-1)

-continued

```
    (xi) SEQUENCE DESCRIPTION: SEQ ID NO:6:

Ala Lys Val Gln Arg Lys Leu Lys Gly Ala Gly Gln Ser Ser Pro Ala
1               5                   10                  15

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (human eIF-4  gamma, aa 471-493,
             GENBANK ACCESSION NO: D12686)

(xi) SEQUENCE DESCRIPTION: SEQ ID NO:7:

Thr Pro Ser Phe Ala Asn Leu Gly Arg Thr Thr Leu Ser Thr Arg Gly
1               5                   10                  15

Pro Pro Arg Gly Gly Pro Gly
            20

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (vii) IMMEDIATE SOURCE: Table 3 (rabbit eIF-4 gamma, aa 472-494,
             GENBANK ACCESSION NO: L22090)

(xi) SEQUENCE DESCRIPTION: SEQ ID NO:8:

Thr Pro Ser Phe Ala Asn Leu Gly Arg Pro Ala Leu Ser Ser Arg Gly
1               5                   10                  15

Pro Pro Arg Gly Gly Pro Gly
            20
```